United States Patent
Deno et al.

(10) Patent No.: US 9,173,586 B2
(45) Date of Patent: *Nov. 3, 2015

(54) SYSTEM AND METHOD FOR ASSESSING COUPLING BETWEEN AN ELECTRODE AND TISSUE

(71) Applicant: St. Jude Medical, Atrial Fibrillation Division, Inc., St. Paul, MN (US)

(72) Inventors: Don Curtis Deno, Andover, MN (US); Stephan P. Miller, Vadnais Heights, MN (US); Lewis C. Hill, Minneapolis, MN (US); Yuriy Malinin, Edina, MN (US); Haris J. Sih, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/777,580

(22) Filed: Feb. 26, 2013

(65) Prior Publication Data
US 2014/0107430 A1    Apr. 17, 2014

Related U.S. Application Data

(63) Continuation of application No. 12/650,060, filed on Dec. 30, 2009, now Pat. No. 8,406,866, which is a
(Continued)

(51) Int. Cl.
*A61B 5/05* (2006.01)
*A61B 5/053* (2006.01)
(Continued)

(52) U.S. Cl.
CPC .............. *A61B 5/053* (2013.01); *A61B 5/6885* (2013.01); *A61B 5/6886* (2013.01);
(Continued)

(58) Field of Classification Search
CPC ...... A61B 5/053; A61B 5/068; A61B 5/6886; A61B 18/14; A61B 2018/00875; A61B 2019/465

USPC ................ 600/424, 508, 547; 606/32; 702/65
See application file for complete search history.

(56) References Cited

U.S. PATENT DOCUMENTS 2,184,511 A    12/1939    Bagno et al.
3,316,896 A    5/1967    Thomasset
(Continued)

FOREIGN PATENT DOCUMENTS

EP    1472976    11/2004
EP    1586281    4/2009
(Continued)

OTHER PUBLICATIONS

International Search Report and Written Opinion issued in international application PCT/US2011/047235 (Dec. 14, 2011).
(Continued)

*Primary Examiner* — Gerald Landry, II
(74) *Attorney, Agent, or Firm* — Dykema Gossett PLLC

(57) ABSTRACT

A system and method for assessing a degree of coupling between an electrode and tissue in a body is provided. Values for first and second components of a complex impedance (e.g., resistance and reactance or impedance magnitude and phase angle) between the electrode and the tissue are obtained. These values are used together with a standardization value indicative of a deviation from a reference standard by a parameter associated with at least one of the body, the electrode and another component of the system to calculate a coupling index that is indicative of a degree of coupling between the electrode and the tissue. The coupling index may be displayed to a clinician in a variety of ways to indicate the degree of coupling to the clinician. The system and method find particular application in ablation of tissue by permitting a clinician to create lesions in the tissue more effectively and safely.

24 Claims, 7 Drawing Sheets

Related U.S. Application Data continuation-in-part of application No. 12/253,637, filed on Oct. 17, 2008, now Pat. No. 8,449,535, which is a continuation-in-part of application No. 12/095,688, filed as application No. PCT/US2006/061714 on Dec. 6, 2006.

(60) Provisional application No. 60/748,234, filed on Dec. 6, 2005.

(51) Int. Cl.
*A61B 5/00* (2006.01)
*A61B 18/12* (2006.01)
*A61B 18/14* (2006.01)
*A61B 18/00* (2006.01)
*A61B 19/00* (2006.01)

(52) U.S. Cl.
CPC ........ *A61B 18/1492* (2013.01); *A61B 18/1233* (2013.01); *A61B 18/14* (2013.01); *A61B 2018/00178* (2013.01); *A61B 2018/00875* (2013.01); *A61B 2019/465* (2013.01)

(56) References Cited

U.S. PATENT DOCUMENTS

| | | |
|---|---|---|
| 3,949,736 A | 4/1976 | Vrana et al. |
| 4,641,649 A | 2/1987 | Walinsky et al. |
| 5,230,349 A | 7/1993 | Langberg |
| 5,257,635 A | 11/1993 | Langberg |
| 5,297,549 A | 3/1994 | Beatty et al. |
| 5,311,866 A | 5/1994 | Kagan et al. |
| 5,341,807 A | 8/1994 | Nardella |
| 5,366,896 A | 11/1994 | Margrey et al. |
| 5,423,808 A | 6/1995 | Edwards et al. |
| 5,429,131 A | 7/1995 | Scheinman |
| 5,447,529 A | 9/1995 | Marchlinski et al. |
| 5,546,940 A | 8/1996 | Panescu et al. |
| 5,562,721 A | 10/1996 | Marchlinski et al. |
| 5,582,609 A | 12/1996 | Swanson et al. |
| 5,588,432 A | 12/1996 | Crowley et al. |
| 5,630,034 A | 5/1997 | Oikawa |
| 5,657,755 A | 8/1997 | Desai |
| 5,659,624 A | 8/1997 | Fazzari |
| 5,673,704 A | 10/1997 | Marchlinski et al. |
| 5,688,267 A | 11/1997 | Panescu |
| 5,697,377 A | 12/1997 | Wittkampf |
| 5,702,386 A | 12/1997 | Stern et al. |
| 5,718,241 A | 2/1998 | Ben-Haim et al. |
| 5,722,402 A | 3/1998 | Swanson |
| 5,730,127 A | 3/1998 | Avitall |
| 5,759,159 A | 6/1998 | Masreliez |
| 5,782,900 A | 7/1998 | de la Rama |
| 5,800,350 A | 9/1998 | Coppleson |
| 5,810,742 A | 9/1998 | Pearlman |
| 5,814,043 A | 9/1998 | Shapeton |
| 5,836,943 A | 11/1998 | Miller, III |
| 5,836,990 A | 11/1998 | Li |
| 5,837,001 A | 11/1998 | Mackey |
| 5,846,238 A | 12/1998 | Jackson et al. |
| 5,904,709 A | 5/1999 | Arndt |
| 5,944,022 A | 8/1999 | Nardella et al. |
| 5,954,665 A | 9/1999 | Ben-Haim |
| 6,001,093 A | 12/1999 | Swanson et al. |
| 6,019,757 A | 2/2000 | Scheldrup |
| 6,026,323 A | 2/2000 | Skladnev |
| 6,035,341 A | 3/2000 | Nunally |
| 6,063,078 A | 5/2000 | Wittkampf |
| 6,129,669 A | 10/2000 | Panescu et al. |
| 6,171,304 B1 | 1/2001 | Netherly |
| 6,179,824 B1 | 1/2001 | Eggers et al. |
| 6,206,874 B1 | 3/2001 | Ubby |
| 6,217,574 B1 | 4/2001 | Webster |
| 6,217,576 B1 | 4/2001 | Tu |
| 6,221,070 B1 | 4/2001 | Tu et al. |
| 6,226,542 B1 | 5/2001 | Reisfeld |
| 6,233,476 B1 | 5/2001 | Strommer et al. |
| 6,246,896 B1 | 6/2001 | Dumoulin et al. |
| 6,256,540 B1 | 7/2001 | Panescu et al. |
| 6,322,558 B1 | 11/2001 | Taylor et al. |
| 6,337,994 B1 | 1/2002 | Stoianovici et al. |
| 6,391,024 B1 | 5/2002 | Sun et al. |
| 6,423,057 B1 | 7/2002 | He et al. |
| 6,427,089 B1 | 7/2002 | Knowlton |
| 6,443,894 B1 | 9/2002 | Sumanaweera et al. |
| 6,445,952 B1 | 9/2002 | Manrodt et al. |
| 6,456,864 B1 | 9/2002 | Swanson et al. |
| 6,471,693 B1 | 10/2002 | Carroll et al. |
| 6,475,215 B1 | 11/2002 | Tanrisever |
| 6,490,474 B1 | 12/2002 | Willis et al. |
| 6,498,944 B1 | 12/2002 | Ben-Haim et al. |
| 6,507,751 B2 | 1/2003 | Blume et al. |
| 6,511,478 B1 | 1/2003 | Burnside et al. |
| 6,558,382 B2 | 5/2003 | Jahns et al. |
| 6,569,160 B1 | 5/2003 | Goldin |
| 6,575,969 B1 | 6/2003 | Rittman, III et al. |
| 6,605,082 B2 | 8/2003 | Hareyama et al. |
| 6,652,518 B2 | 11/2003 | Wellman et al. |
| 6,663,622 B1 | 12/2003 | Foley et al. |
| 6,683,280 B1 | 1/2004 | Wofford |
| 6,690,963 B2 | 2/2004 | Ben-Haim et al. |
| 6,696,844 B2 | 2/2004 | Wong et al. |
| 6,712,074 B2 | 3/2004 | Edwards et al. |
| 6,743,225 B2 | 6/2004 | Sanchez et al. |
| 6,755,790 B2 | 6/2004 | Stewart et al. |
| 6,780,182 B2 | 8/2004 | Bowman et al. |
| 6,788,967 B2 | 9/2004 | Ben-Haim et al. |
| 6,813,515 B2 | 11/2004 | Hashimshony |
| 6,840,938 B1 | 1/2005 | Morley et al. |
| 6,917,834 B2 * | 7/2005 | Koblish et al. ............. 607/122 |
| 6,918,876 B1 | 7/2005 | Kamiyama |
| 6,926,669 B1 | 8/2005 | Stewart |
| 6,936,047 B2 | 8/2005 | Nasab et al. |
| 6,950,689 B1 | 9/2005 | Willis et al. |
| 6,964,867 B2 | 11/2005 | Downs |
| 6,965,795 B2 | 11/2005 | Rock |
| 6,993,384 B2 | 1/2006 | Bradley et al. |
| 7,041,095 B2 | 5/2006 | Wang et al. |
| 7,041,096 B2 | 5/2006 | Malis |
| 7,106,043 B1 | 9/2006 | Da Silva |
| 7,197,354 B2 | 3/2007 | Sobe |
| 7,248,032 B1 | 7/2007 | Hular |
| 7,263,395 B2 | 8/2007 | Chan et al. |
| 7,263,397 B2 | 8/2007 | Hauck et al. |
| 7,386,339 B2 | 6/2008 | Strommer et al. |
| 7,497,858 B2 | 3/2009 | Chapelon et al. |
| 7,499,745 B2 | 3/2009 | Littrup |
| 7,536,218 B2 | 5/2009 | Govari et al. |
| 7,565,613 B2 | 7/2009 | Forney |
| 7,610,078 B2 | 10/2009 | Willis |
| 7,633,502 B2 | 12/2009 | Willis et al. |
| 7,671,871 B2 | 3/2010 | Gonsalves |
| 7,776,034 B2 | 8/2010 | Kampa |
| 7,819,870 B2 | 10/2010 | Thao et al. |
| 7,865,236 B2 | 1/2011 | Cory |
| 7,904,174 B2 | 3/2011 | Hammill et al. |
| 7,953,495 B2 | 5/2011 | Sommer et al. |
| 2001/0034501 A1 | 10/2001 | Tom |
| 2001/0039413 A1 | 11/2001 | Bowe |
| 2001/0047129 A1 | 11/2001 | Hall |
| 2001/0051774 A1 | 12/2001 | Littrup et al. |
| 2002/0022836 A1 | 2/2002 | Goble et al. |
| 2002/0049375 A1 | 4/2002 | Strommer et al. |
| 2002/0068931 A1 | 6/2002 | Wong et al. |
| 2002/0072686 A1 | 6/2002 | Hoey et al. |
| 2002/0077627 A1 | 6/2002 | Johnson et al. |
| 2002/0120188 A1 | 8/2002 | Brock et al. |
| 2002/0123749 A1 | 9/2002 | Jain |
| 2002/0177847 A1 | 11/2002 | Long |
| 2003/0004587 A1 | 1/2003 | Raymond et al. |
| 2003/0028183 A1 | 2/2003 | Sanchez et al. |
| 2003/0045871 A1 * | 3/2003 | Jain et al. ............. 606/41 |
| 2003/0060696 A1 | 3/2003 | Skladnev et al. |

(56) References Cited

U.S. PATENT DOCUMENTS

| | | |
|---|---|---|
| 2003/0065364 A1 | 4/2003 | Wellman et al. |
| 2003/0093067 A1 | 5/2003 | Panescu |
| 2003/0093069 A1 | 5/2003 | Panescu et al. |
| 2003/0100823 A1 | 5/2003 | Kipke et al. |
| 2003/0109871 A1 | 6/2003 | Johnson et al. |
| 2003/0130711 A1 | 7/2003 | Pearson et al. |
| 2003/0187430 A1 | 10/2003 | Vorisek |
| 2004/0006337 A1 | 1/2004 | Nasab et al. |
| 2004/0030258 A1 | 2/2004 | Williams et al. |
| 2004/0044292 A1 | 3/2004 | Yasushi et al. |
| 2004/0078036 A1 | 4/2004 | Keidar |
| 2004/0078058 A1 | 4/2004 | Holmstrom et al. |
| 2004/0082946 A1 | 4/2004 | Malis et al. |
| 2004/0087975 A1 | 5/2004 | Lucatero et al. |
| 2004/0097806 A1 | 5/2004 | Hunter |
| 2004/0147920 A1 | 7/2004 | Keidar |
| 2004/0181165 A1 | 9/2004 | Hoey |
| 2004/0243018 A1 | 12/2004 | Organ et al. |
| 2004/0243181 A1 | 12/2004 | Conrad |
| 2004/0267252 A1 | 12/2004 | Washington |
| 2005/0010263 A1 | 1/2005 | Schauerte |
| 2005/0054944 A1 | 3/2005 | Nakada et al. |
| 2005/0065507 A1 | 3/2005 | Hartley |
| 2005/0222554 A1 | 10/2005 | Wallace et al. |
| 2006/0015033 A1 | 1/2006 | Blakley et al. |
| 2006/0085049 A1 | 4/2006 | Cory et al. |
| 2006/0173251 A1 | 8/2006 | Govari |
| 2006/0200049 A1 | 9/2006 | Leo et al. |
| 2006/0235286 A1 | 10/2006 | Stone |
| 2007/0016006 A1 | 1/2007 | Shachar |
| 2007/0055142 A1 | 3/2007 | Webler |
| 2007/0073179 A1 | 3/2007 | Alonso et al. |
| 2007/0083193 A1 | 4/2007 | Werneth et al. |
| 2007/0100332 A1 | 5/2007 | Paul et al. |
| 2007/0106289 A1 | 5/2007 | O'Sullivan |
| 2007/0123764 A1 | 5/2007 | Thao et al. |
| 2007/0161915 A1 | 7/2007 | Desai |
| 2007/0225558 A1 | 9/2007 | Hauck et al. |
| 2007/0225593 A1 | 9/2007 | Porath |
| 2007/0244479 A1 | 10/2007 | Beatty et al. |
| 2007/0255162 A1 | 11/2007 | Abboud et al. |
| 2008/0091193 A1 | 4/2008 | Kauphusman |
| 2008/0097220 A1 | 4/2008 | Lieber |
| 2008/0097422 A1 | 4/2008 | Edwards et al. |
| 2008/0132890 A1 | 6/2008 | Woloszko |
| 2008/0183071 A1 | 7/2008 | Strommer et al. |
| 2008/0183189 A1 | 7/2008 | Teichman et al. |
| 2008/0221440 A1 | 9/2008 | Iddan et al. |
| 2008/0234564 A1 | 9/2008 | Beatty et al. |
| 2008/0249536 A1 | 10/2008 | Stahler |
| 2008/0275465 A1 | 11/2008 | Paul et al. |
| 2008/0288023 A1 | 11/2008 | John |
| 2008/0288038 A1 | 11/2008 | Paul et al. |
| 2008/0300589 A1* | 12/2008 | Paul et al. ............... 606/34 |
| 2008/0312713 A1 | 12/2008 | Wilfey |
| 2009/0012533 A1 | 1/2009 | Barbagli |
| 2009/0036794 A1 | 2/2009 | Stubhaug et al. |
| 2009/0163904 A1 | 6/2009 | Miller et al. |
| 2009/0171235 A1 | 7/2009 | Schneider et al. |
| 2009/0171345 A1 | 7/2009 | Miller et al. |
| 2009/0177111 A1 | 7/2009 | Miller et al. |
| 2009/0247942 A1 | 10/2009 | Kirschenman |
| 2009/0247943 A1 | 10/2009 | Kirschenman |
| 2009/0247944 A1 | 10/2009 | Kirschenman |
| 2009/0247993 A1 | 10/2009 | Kirschenman et al. |
| 2009/0248042 A1 | 10/2009 | Kirschenman |
| 2009/0275827 A1* | 11/2009 | Aiken et al. .............. 600/424 |
| 2009/0276002 A1 | 11/2009 | Sommer et al. |
| 2009/0306655 A1 | 12/2009 | Stangenes |
| 2010/0069921 A1 | 3/2010 | Miller et al. |
| 2010/0168550 A1* | 7/2010 | Byrd et al. ............... 600/407 |
| 2010/0168735 A1 | 7/2010 | Deno et al. |
| 2010/0191089 A1* | 7/2010 | Stebler et al. ............ 600/373 |
| 2010/0256558 A1 | 10/2010 | Olson et al. |
| 2010/0274239 A1* | 10/2010 | Paul et al. ............... 606/33 |
| 2010/0298823 A1 | 11/2010 | Cao et al. |
| 2011/0015569 A1 | 1/2011 | Kirschenman |
| 2011/0118727 A1 | 5/2011 | Fish et al. |
| 2011/0313311 A1* | 12/2011 | Gaw ......................... 600/547 |
| 2011/0313417 A1 | 12/2011 | De La Rama et al. |
| 2012/0158011 A1 | 6/2012 | Sandhu |

FOREIGN PATENT DOCUMENTS

| | | |
|---|---|---|
| JP | H08511440 | 12/1996 |
| JP | 3585491 | 11/2004 |
| JP | 2005279256 | 10/2005 |
| WO | WO-98/46149 | 10/1998 |
| WO | WO-00/78239 | 12/2000 |
| WO | WO-2007/067941 | 6/2007 |
| WO | WO-2009/065140 | 5/2009 |
| WO | WO-2009/085457 | 7/2009 |
| WO | 2009/120982 | 10/2009 |
| WO | 2011/123669 | 10/2011 |

OTHER PUBLICATIONS

International Search Report and Written Opinion issued in international application PCT/US2006/061714 (Sep. 22, 2008).

International Search Report and Written Opinion issued in international application PCT/US2008/084194 (Feb. 5, 2009).

Avitall, Boaz et al., "The Effects of Electrode-Tissue Contact on Radiofrequency Lesion Generation", PACE, vol. 20, Dec. 1997, 2899-2910.

Chakraborty, D. P., "ROC curves predicted by a model of visual search", Institute of Physics Publishing, Phys. Med. Biol. 51, 2006, 3463-3482.

Cho, Sungbo et al., "Design of electrode array for impedance measurement of lesions in arteries", Physiol. Meas. 26 S19-S26, doi: 10.1088/0967-3334/26/2/002, 2005.

Dumas, John H. et al., "Myocardial electrical impedance as a predictor of the quality of RF-induced linear lesions", Physiological Measurement, vol. 29, 2008, Abstract only.

Fenici, R. R. et al., "Biomagnetically localizable multipurpose catheter and method for MCG guided intracardiac electrophysiology, biopsy and ablation of cardiac arrhythmias", International Journal of Cardiac Imaging 7, 1991, 207-215.

Gales, Rosemary et al., "Use of bioelectrical impedance analysis to assess body composition of seals", Marine Mammal Science, vol. 10, Issue 1, Abstract, Aug. 26, 2006.

Gao, Xin et al., "Computer-Assisted Quantative Evaluation of Therapeutic Responses for Lymphoma Using Serial PET/CT Imaging", NIH Public Access, Acad Radiol. 17(4), Apr. 2010, 1-21.

He, Ding S. et al., "Assessment of Myocardial Lesion Size during In Vitro Radio Frequency Catheter Ablation", IEEE Transactions on Biomedical Engineering, vol. 50, No. 6, Jun. 2003, 768-776.

Himel, Herman D., "Development of a metric to assess completeness of lesions produced by radiofrequency ablation in the heart", Dept. of Biomedical Engineering, University of NC, Chapel Hill, 2006, i-xvii; 1-138.

Holmes, Douglas et al., "Tissue Sensing Technology Enhances Lesion Formation During Irrigated Catheter Ablation", HRS, 2008, Abstract only.

Masse, Stephane et al., "A Three-dimensional display for cardiac activation mapping", Pace, vol. 14, Apr. 1991.

Salazar, Y et al., "Transmural versus nontransmural in situ electrical impedance spectrum for healthy, ischemic, and healed myocardium", IEEE Xplore, Abstract, 2009.

Zheng, Xiangsheng et al., "Electrode Impedance: An Indicator of Electrode-Tissue Contact and Lesion Dimensions During Linear Ablation", Journal of Interventional Cardiac Electrophysiology 4.4, pp. 645-654 (2000).

Thomas, Stuart P., et al., Comparison of Epicardial and Endocardial Linear Ablation Using Handheld Probes, The Annals of Thoracic Surgery, vol. 75, Issue 2, pp. 543-548, Feb. 2003.

Supplementary European Search Report issued in EP Patent Application No. 11842330.0 (Jan. 20, 2014).

International Search Report for PCT Application No. PCT/US2006/046565, dated May 2, 2007, 1 page.

(56) References Cited

OTHER PUBLICATIONS

International Search Report and Written Opinion for PCT Application No. PCT/US2006/061716, dated Oct. 4, 2007, 7 pages.
International Search Report and Written Opinion for PCT Application No. PCT/US2006/061712, dated Oct. 29, 2007, 7 pages.
International Search Report and Written Opinion for PCT Application No. PCT/US2006/061710, dated Feb. 15, 2008, 10 pages.
International Search Report and Written Opinion for PCT Application No. PCT/US2006/061711, dated Oct. 5, 2007, 8 pages.
International Search Report and Written Opinion for PCT Application No. PCT/US2006/061713, dated Oct. 3, 2007, 1 page.
International Search Report and Written Opinion for PCT Application No. PCT/US2006/061717, dated Oct. 4, 2007, 9 pages.
Supplementary European Search Report for EP Application No. 06839102.8, dated Nov. 16, 2009, 7 pages.
Supplementary European Search Report for EP Application No. 06848530.9, dated Nov. 17, 2009, 7 pages.
Supplementary European Search Report for EP Application No. 06840133.0, dated Nov. 16, 2009, 8 pages.
International Search Report and Written Opinion for PCT Application No. PCT/US2010/034412, dated Jun. 29, 2010, 1 page.
Supplementary European Search Report for EP Application No. 10775417.8, dated Oct. 25, 2013, 5 pages.
International Search Report and Written Opinion for PCT Application No. PCT/US2008/084200, dated Jan. 22, 2009, 1 page.
International Search Report and Written Opinion for PCT Application No. PCT/US2010/034414, dated Sep. 1, 2010, 13 pages.

\* cited by examiner

SYSTEM AND METHOD FOR ASSESSING COUPLING BETWEEN AN ELECTRODE AND TISSUE

CROSS REFERENCE TO RELATED APPLICATIONS

This application is a continuation of U.S. application Ser. No. 12/650,060, filed 30 Dec. 2009 (the '060 application), now pending, which is a continuation-in-part of U.S. patent application Ser. No. 12/253,637 filed Oct. 17, 2008 (the '637 application), which is a continuation-in-part of U.S. patent application Ser. No. 12/095,688 filed May 30, 2008 (the '688 application), which is a national stage application of International application no. PCT/US2006/061714 filed Dec. 6, 2006 (the '714 application) which claims the benefit of U.S. Provisional patent application No. 60/748,234 filed Dec. 6, 2005 (the '234 application). The '060 application, the '637 application, the '688 application, the '714 application and the '234 application are all hereby incorporated by reference as though fully set forth herein.

BACKGROUND OF THE INVENTION a. Field of the Invention

This invention relates to a system and method for assessing the degree of coupling between an electrode and tissue in a body. In particular, the instant invention relates to a system and method for assessing the degree of electrical coupling between electrodes on an diagnostic and/or therapeutic medical device such as a mapping or ablation catheter and tissue, such as cardiac tissue.

b. Background Art

Electrodes are used on a variety of diagnostic and/or therapeutic medical devices. For example, electrodes may be used on cardiac mapping catheters to generate an image of the internal geometry of a heart and electrical potentials within the tissue. Electrodes are also used on ablation catheters to create tissue necrosis in cardiac tissue to correct conditions such as atrial arrhythmia (including, but not limited to, ectopic atrial tachycardia, atrial fibrillation, and atrial flutter). Arrhythmia can create a variety of dangerous conditions including irregular heart rates, loss of synchronous atrioventricular contractions and stasis of blood flow which can lead to a variety of ailments and even death. It is believed that the primary cause of atrial arrhythmia is stray electrical signals within the left or right atrium of the heart. The ablation catheter imparts ablative energy (e.g., radiofrequency energy, cryoablation, lasers, chemicals, high-intensity focused ultrasound, etc.) to cardiac tissue to create a lesion in the cardiac tissue. This lesion disrupts undesirable electrical pathways and thereby limits or prevents stray electrical signals that lead to arrhythmias.

The safety and effectiveness of many of diagnostic and/or therapeutic devices is often determined in part by the proximity of the device and the electrodes to the target tissue. In mapping catheters, the distance between the electrodes and the target tissue affects the strength of the electrical signal and the identity of the mapping location. The safety and effectiveness of ablation lesions is determined in part by the proximity of the ablation electrode to target tissue and the effective application of energy to that tissue. If the electrode is too far from the tissue or has insufficient contact with the tissue, the lesions created may not be effective. On the other hand, if the catheter tip containing the electrode contacts the tissue with excessive force, the catheter tip may perforate or otherwise damage the tissue (e.g., by overheating). It is therefore beneficial to assess the quality of contact between the electrode and the tissue.

Contact between a catheter electrode and tissue has typically been determined using one or more of the following methods: clinician sense, fluoroscopic imaging, intracardiac echo (ICE), atrial electrograms (typically bipolar D-2), pacing thresholds, evaluation of lesion size at necropsy and measurement of temperature change at the energy delivery site. Each of these methods has disadvantages, however.

Although a clinician can evaluate contact based on tactile feedback from the catheter and prior experience, the determination depends largely on the experience of the clinician and is also subject to change based on variations in the mechanical properties of catheters used by the clinician. The determination is particularly difficult when using catheters that are relatively long (such as those used to enter the left atria of the heart).

Because fluoroscopic images are two-dimensional projections and blood and myocardium attenuate x-rays similarly, it is difficult to quantify the degree of contact and to detect when the catheter tip is not in contact with the tissue. Fluoroscopic imaging also exposes the patient and clinician to radiation.

Intracardiac echo is time consuming and it is also difficult to align the echo beam with the ablation catheter. Further, intracardiac echo does not always permit the clinician to confidently assess the degree of contact and can generate unacceptable levels of false positives and false negatives in assessing whether the electrode is in contact with tissue.

Atrial electrograms do not always correlate well to tissue contact and are also prone to false negatives and positives. Pacing thresholds also do not always correlate well with tissue contact and pacing thresholds are time-consuming and also prone to false positives and false negatives because tissue excitability may vary in hearts with arrhythmia. Evaluating lesion size at necropsy is seldom available in human subjects, provides limited information (few data points) and, further, it is often difficult to evaluate the depth and volume of lesions in the left and right atria. Finally, temperature measurements provide limited information (few data points) and are difficult to evaluate in the case of irrigated catheters.

A more recent method of assessing contact between the catheter electrode and tissue is the use of force sensors incorporated into the catheter to measure contact force between the catheter tip and tissue. Contact force, however, does not directly measure how well electrical energy is coupled between the catheter electrode and tissue. Particularly for radio-frequency (RF) ablation catheters, a measure of electrical coupling may be more relevant to ablation safety and efficacy in different types of tissue and in different types of catheter tip to tissue surface alignment (e.g., perpendicular versus parallel orientation). The use of force sensors also requires significant structural adjustments and technological advances for use in conventional ablation catheters.

Contact between the catheter electrode and tissue has also been evaluated by measuring impedance between the catheter electrode and an electrode disposed on the a patient's skin. During radio frequency (RF) ablation, the generation of RF energy is controlled by an ablation generator. The ablation generator displays a measure of the magnitude of impedance (Z). This measurement, however, does not correlate well with the more localized contact between the catheter electrode and tissue because it measures the impedance provided not just by the local target tissue, but the entire impedance from the electrode to a cutaneous return electrode through various body tissues and fluids. Furthermore, generator reported impedance is usually infrequently obtained and at low resolution (about 1Ω). It is also not readily available to the clinician in a format that allows easy interpretation and correlation to tissue contact.

In priority U.S. patent application Ser. No. 12/253,637, a system and method are provided for determining a degree of coupling between a catheter electrode and tissue in which an electrical coupling index (ECI) is generated as an indicator of impedance at the interface of the electrode and the target tissue. Because the coupling index is indicative of impedance at the interface of the electrode and target tissue, the inventive system and method provide a better assessment of coupling between the electrode and the tissue and the index permits a better assessment of the degree of coupling between an electrode and tissue as compared to prior art systems. The index, however, is subject to variability based on changes to properties associated with patient bodies (e.g. differences in body temperature among patients) and components of the system (e.g., differences resulting from the use of different ablation catheters).

The inventors herein have recognized a need for a system and method for determining a degree of coupling between a catheter electrode and tissue that will minimize and/or eliminate one or more of the above-identified deficiencies.

BRIEF SUMMARY OF THE INVENTION

It is desirable to provide a system and method for determining the degree of coupling between an electrode and a tissue in a body. In particular, it is desirable to be able to determine a degree of electrical coupling between electrodes on an diagnostic and/or therapeutic medical device such as a mapping or ablation catheter and tissue, such as cardiac tissue.

A system for assessing a degree of coupling between an electrode and a tissue in a body in accordance with one embodiment of the present invention includes an electronic control unit configured to acquire values for first and second components of a complex impedance between the electrode and the tissue. The first and second components may comprise, for example, a resistance between the electrode and the tissue and a reactance between the electrode and the tissue. Alternatively, the first and second components may comprise an impedance magnitude between the electrode and the tissue and an impedance phase angle. The electronic control unit is further configured to calculate a coupling index responsive to the values and a standardization value indicative of a deviation from a reference standard by a parameter associated with at least one of the body, the electrode and another component of the system. The standardization value may, for example, be indicative of a difference in body temperature in a patient relative to a reference or standard temperature or a difference in the size of the electrode relative to a reference or standard electrode size. The coupling index is indicative of a degree of coupling between the electrode and the tissue. In accordance with one aspect of the invention, the coupling index may be displayed to a clinician on a display device in a variety of ways to provide to permit easy interpretation and correlation of the measured impedance to coupling between the electrode and tissue.

Similarly, an article of manufacture for assessing a degree of coupling between an electrode and a tissue in a body in accordance with another embodiment of the present invention includes a computer storage medium having a computer program encoded thereon for determining a degree of coupling between an electrode and tissue in a body. The computer program includes code for calculating a coupling index responsive to values for first and second components of a complex impedance between the electrode and the tissue and a standardization value indicative of a deviation from a reference standard by a parameter associated with at least one of the body, the electrode and another component of a system controlling the electrode. The coupling index is indicative of a degree of coupling between the electrode and the tissue.

A method for assessing a degree of coupling between an electrode and a tissue in a body in accordance with another embodiment of the present invention includes the step of acquiring values for first and second components of a complex impedance between the electrode and the tissue. Again, the first and second components may comprise, for example, a resistance between the electrode and the tissue and a reactance between the electrode and the tissue. Alternatively, the first and second components may comprise an impedance magnitude between the electrode and the tissue and an impedance phase angle. The method further includes the step of calculating a coupling index responsive to the values and a standardization value indicative of a deviation from a reference standard by a parameter associated with at least one of the body, the electrode and another component of a system controlling the electrode. The coupling index is indicative of a degree of coupling between the electrode and the tissue.

The above-described system, article of manufacture and method are advantageous because they provide a true measure of impedance at the interface of the electrode and the target tissue and, therefore, provide a better assessment of coupling between the electrode and the tissue. Moreover, the measurement is standardized such that it will provide a similar measure despite variation in parameters associated with the body, the electrode, and the system as a whole. Further, the system, article of manufacture and method provide an indicator of coupling (i.e., the coupling index) in a format that allows easy interpretation and correlation to tissue contact by the clinician.

The coupling index can be used in a wide variety of diagnostic and therapeutic devices. In ablation catheters, for example, procedures can be conducted more efficiently and with higher success rates and fewer complications because the coupling index provides an indication of the energy delivered to the target tissue and the proximity of the catheter and electrode to the target tissue and may also enable a clinician to identify the orientation or angle of the ablation electrode relative to the tissue. The index also can act as a proximity sensor indicating the distance between a diagnostic or therapeutic device and a target tissue. For example, in a transseptal access sheath, the coupling index provides an indication that the sheath is approaching (and potentially slipping away from) the septum. In a mapping catheter, the coupling index may improve geometric modeling of the tissue surface by, for example, identifying the most relevant electrode readings and/or allowing multiple electrodes to simultaneously obtain relevant measurements.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 1:
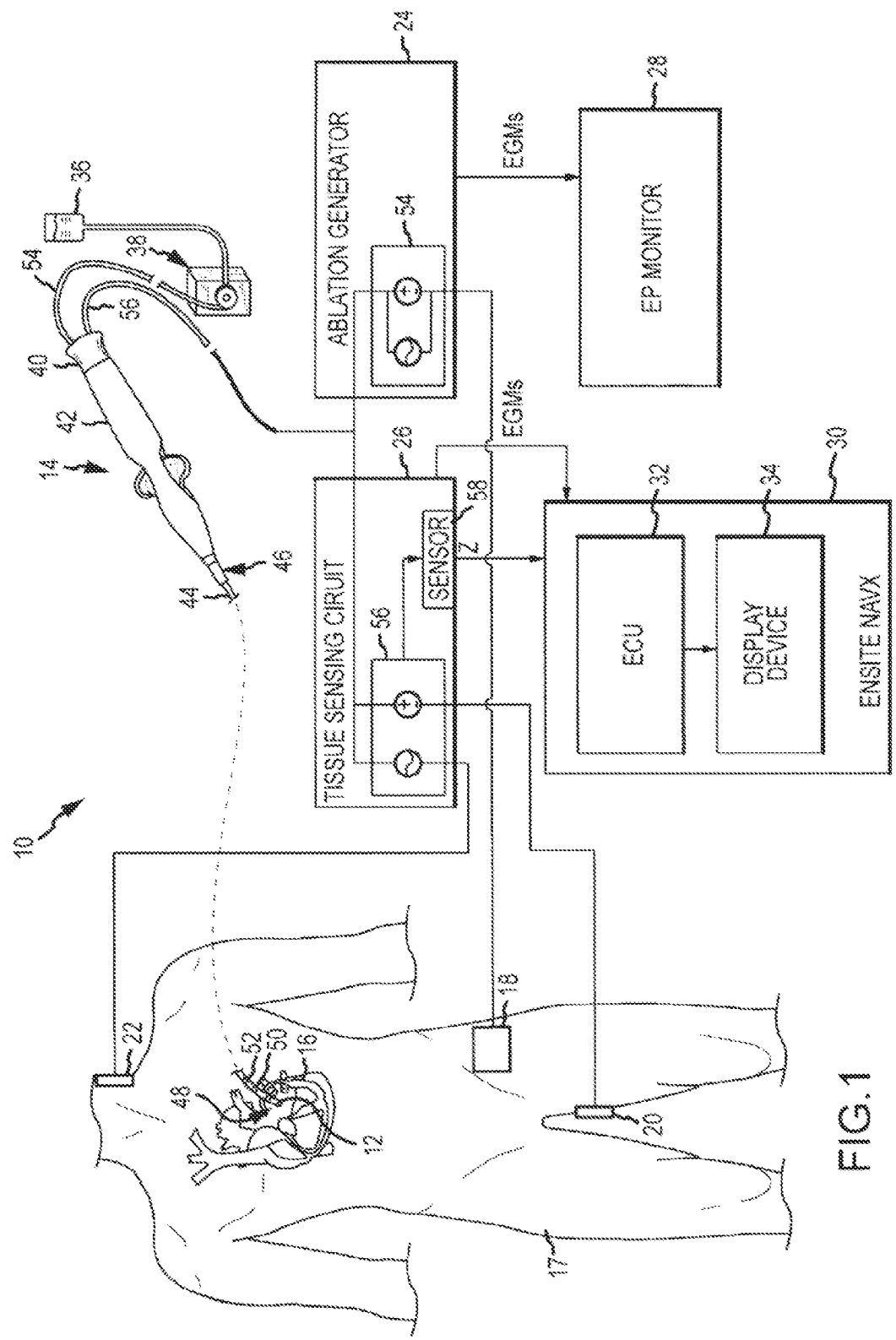
FIG. 1 is diagrammatic view of a system in accordance with the present teachings.

Referring now to the drawings wherein like reference numerals are used to identify identical components in the various views, FIG. 1 illustrates one embodiment of a system 10 for one or more diagnostic and therapeutic functions including components providing an improved assessment of a degree of coupling between an electrode 12 on a catheter 14 and a tissue 16 in a body 17. In the illustrated embodiment, tissue 16 comprises heart or cardiac tissue. It should be understood, however, that the present invention may be used to evaluate coupling between electrodes and a variety of body tissues. Further, although electrode 12 is illustrated as part of a catheter 14, it should be understood that the present invention may be used to assess a degree of coupling between any type of electrode and tissue including, for example, intracardiac electrodes, needle electrodes, patch electrodes, wet brush electrodes (such as the electrodes disclosed in commonly assigned U.S. patent application Ser. No. 11/190,724 filed Jul. 27, 2005, the entire disclosure of which is incorporated herein by reference) and virtual electrodes (e.g., those formed from a conductive fluid medium such as saline including those disclosed in commonly assigned U.S. Pat. No. 7,326,208 issued Feb. 5, 2008, the entire disclosure of which is incorporated herein by reference). In addition to catheter 14, system 10 may include patch electrodes 18, 20, 22, an ablation generator 24, a tissue sensing circuit 26, an electrophysiology (EP) monitor 28 and a system 30 for visualization, mapping and navigation of internal body structures which may include an electronic control unit 32 in accordance with the present invention and a display device 34 among other components.

Catheter 14 is provided for examination, diagnosis and treatment of internal body tissues such as tissue 16. In accordance with one embodiment of the invention, catheter 14 comprises an ablation catheter and, more particularly, an irrigated radio-frequency (RF) ablation catheter. It should be understood, however, that the present invention can be implemented and practiced regardless of the type of ablation energy provided (e.g., cryoablation, ultrasound, etc.) Catheter 14 is connected to a fluid source 36 having a biocompatible fluid such as saline through a pump 38 (which may comprise, for example, a fixed rate roller pump or variable volume syringe pump with a gravity feed supply from fluid source 36 as shown) for irrigation. Catheter 14 is also electrically connected to ablation generator 24 for delivery of RF energy. Catheter 14 may include a cable connector or interface 40, a handle 42, a shaft 44 having a proximal end 46 and a distal 48 end (as used herein, "proximal" refers to a direction toward the end of the catheter near the clinician, and "distal" refers to a direction away from the clinician and (generally) inside the body of a patient) and one or more electrodes 12, 50, 52. Catheter 14 may also include other conventional components not illustrated herein such as a temperature sensor, additional electrodes, and corresponding conductors or leads.

Connector 40 provides mechanical, fluid and electrical connection(s) for cables 54, 56 extending from pump 38 and ablation generator 24. Connector 40 is conventional in the art and is disposed at a proximal end of catheter 14.

Handle 42 provides a location for the clinician to hold catheter 14 and may further provides means for steering or guiding shaft 44 within body 17. For example, handle 42 may include means to change the length of a guidewire extending through catheter 14 to distal end 48 of shaft 44 to steer shaft 44. Handle 42 is also conventional in the art and it will be understood that the construction of handle 42 may vary.

Shaft 44 is an elongated, tubular, flexible member configured for movement within body 17. Shaft 44 support electrodes 12, 50, 52 associated conductors, and possibly additional electronics used for signal processing or conditioning. Shaft 44 may also permit transport, delivery and/or removal of fluids (including irrigation fluids and bodily fluids), medicines, and/or surgical tools or instruments. Shaft 44 may be made from conventional materials such as polyurethane and defines one or more lumens configured to house and/or transport electrical conductors, fluids or surgical tools. Shaft 44 may be introduced into a blood vessel or other structure within body 17 through a conventional introducer. Shaft 44 may then be steered or guided through body 17 to a desired location such as tissue 16 with guide wires or other means known in the art.

Electrodes 12, 50, 52 are provided for a variety of diagnostic and therapeutic purposes including, for example, electrophysiological studies, catheter identification and location, pacing, cardiac mapping and ablation. In the illustrated embodiment, catheter includes an ablation tip electrode 12 at distal end 48 of shaft 44 and a pair of ring electrodes 50, 52. It should be understood, however, that the number, orientation and purpose of electrodes 12, 50, 52 may vary.

Patch electrodes 18, 20, 22 provide RF or navigational signal injection paths and/or are used to sense electrical potentials. Electrodes 18, 20, 22 may also have additional purposes such as the generation of an electromechanical map. Electrodes 18, 20, 22 are made from flexible, electrically conductive material and are configured for affixation to body 17 such that electrodes 18, 20, 22 are in electrical contact with the patient's skin. Electrode 18 may function as an RF indifferent/dispersive return for the RF ablation signal. Electrodes 20, 22 may function as returns for the RF ablation signal source and/or an excitation signal generated by tissue sensing circuit 26 as described in greater detail hereinbelow. In accordance with one aspect of the present invention discussed hereinbelow, electrodes 20, 22 are preferably spaced relatively far apart. In the illustrated embodiment, electrodes 20, 22, are located on the medial aspect of the left leg and the dorsal aspect of the neck. Electrodes 20, 22, may alternatively be located on the front and back of the torso or in other conventional orientations.

Ablation generator 24 generates, delivers and controls RF energy used by ablation catheter 14. Generator 24 is conventional in the art and may comprise the commercially available unit sold under the model number IBI-1500T RF Cardiac Ablation Generator, available from Irvine Biomedical, Inc. Generator 24 includes an RF ablation signal source 54 configured to generate an ablation signal that is output across a pair of source connectors: a positive polarity connector SOURCE (+) which may connect to tip electrode 12; and a negative polarity connector SOURCE (−) which may be electrically connected by conductors or lead wires to one of patch electrodes 18, 20, 22 (see FIG. 2). It should be understood that the term connectors as used herein does not imply a particular type of physical interface mechanism, but is rather broadly contemplated to represent one or more electrical nodes. Source 54 is configured to generate a signal at a predetermined frequency in accordance with one or more user specified parameters (e.g., power, time, etc.) and under the control of various feedback sensing and control circuitry as is know in the art. Source 54 may generate a signal, for example, with a frequency of about 450 kHz or greater. Generator 24 may also monitor various parameters associated with the ablation procedure including impedance, the temperature at the tip of the catheter, ablation energy and the position of the catheter and provide feedback to the clinician regarding these parameters. The impedance measurement output by generator 24, however, reflects the magnitude of impedance not only at tissue 16, but the entire impedance between tip electrode 12 and the corresponding patch electrode 18 on the body surface. The impedance output by generator 24 is also not easy to interpret and correlate to tissue contact by the clinician.

Tissue sensing circuit 26 provides a means, such as tissue sensing signal source 56, for generating an excitation signal used in impedance measurements and means, such as complex impedance sensor 58, for resolving the detected impedance into its component parts. Signal source 56 is configured to generate an excitation signal across source connectors SOURCE (+) and SOURCE (−) (See FIG. 2). Source 56 may output a signal having a frequency within a range from about 1 kHz to over 500 kHz, more preferably within a range of about 2 kHz to 200 kHz, and even more preferably about 20 kHz. In one embodiment, the excitation signal is a constant current signal, preferably in the range of between 20-200 μA, and more preferably about 100 μA. As discussed below, the constant current AC excitation signal generated by source 56 is configured to develop a corresponding AC response voltage signal that is dependent on the complex impedance of tissue 16 and is sensed by complex impedance sensor 58. Sensor 58 resolves the complex impedance into its component parts (i.e., the resistance (R) and reactance (X) or the impedance magnitude (|Z|) and phase angle (∠Z or φ)). Sensor 58 may include conventional filters (e.g., bandpass filters) to block frequencies that are not of interest, but permit appropriate frequencies, such as the excitation frequency, to pass as well as conventional signal processing software used to obtain the component parts of the measured complex impedance.

It should be understood that variations are contemplated by the present invention. For example, the excitation signal may be an AC voltage signal where the response signal comprises an AC current signal. Nonetheless, a constant current excitation signal is preferred as being more practical. It should be appreciated that the excitation signal frequency is preferably outside of the frequency range of the RF ablation signal, which allows the complex impedance sensor 58 to more readily distinguish the two signals, and facilitates filtering and subsequent processing of the AC response voltage signal. The excitation signal frequency is also preferably outside the frequency range of conventionally expected electrogram (EGM) signals in the frequency range of 0.05-1 kHz. Thus, in summary, the excitation signal preferably has a frequency that is preferably above the typical EGM signal frequencies and below the typical RF ablation signal frequencies.

Circuit 26 is also connected, for a purpose described hereinbelow, across a pair of sense connectors: a positive polarity connector SENSE (+) which may connect to tip electrode 12; and a negative polarity connector SENSE (−) which may be electrically connected to one of patch electrodes 18, 20, 22 (see FIG. 2; note, however, that the connector SENSE (−) should be connected to a different electrode of electrodes 18, 20, 22 relative to the connector SOURCE (−) as discussed below). It should again be understood that the term connectors as used herein does not imply a particular type of physical interface mechanism, but is rather broadly contemplated to represent one or more electrical nodes.

Figure 2:
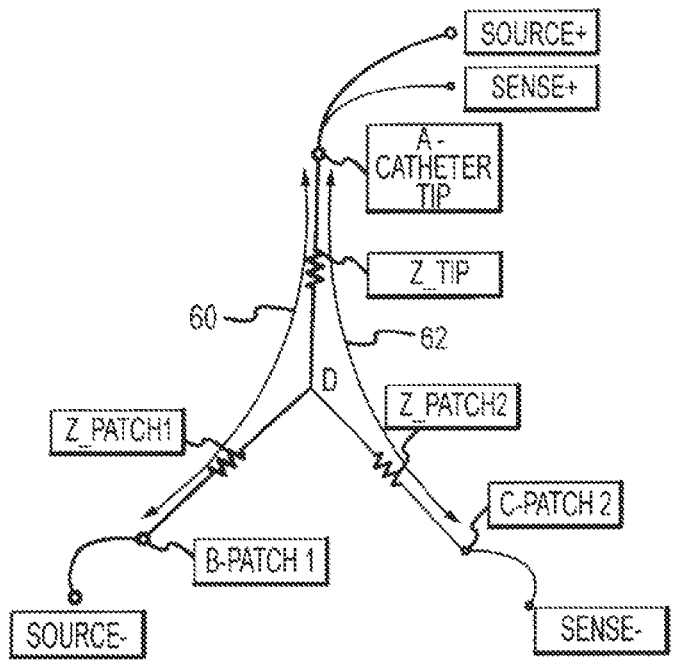
FIG. 2 is a simplified schematic diagram illustrating how impedance is determined in accordance with the present teachings.

Referring now to FIG. 2, connectors SOURCE (+), SOURCE (−), SENSE (+) and SENSE (−) from a three terminal arrangement permitting measurement of the complex impedance at the interface of tip electrode 12 and tissue 16. Complex impedance can be expressed in rectangular coordinates as set forth in equation (1):

$$Z = R + jX \quad (1)$$

where R is the resistance component (expressed in ohms); and X is a reactance component (also expressed in ohms). Complex impedance can also be expressed polar coordinates as set forth in equation (2):

$$Z = r \cdot e^{j\theta} = |Z| \cdot e^{j \angle Z} \quad (2)$$

where |Z| is the magnitude of the complex impedance (expressed in ohms) and ∠Z=θ is the phase angle expressed in radians. Alternatively, the phase angle may be expressed in terms of degrees where $$\phi = \left(\frac{180}{\pi}\right)\theta.$$

Throughout the remainder of this specification, phase angle will be preferably referenced in terms of degrees. The three terminals comprise: (1) a first terminal designated "A-Catheter Tip" which is the tip electrode 12; (2) a second terminal designated "B-Patch 1" such as source return patch electrode 22; and (3) a third terminal designated "C-Patch 2" such as the sense return patch electrode 20. In addition to the ablation (power) signal generated by source 54 of ablation generator 24, the excitation signal generated by source 56 in tissue sensing circuit 26 is also be applied across the source connectors (SOURCE (+), SOURCE (−)) for the purpose of inducing a response signal with respect to the load that can be measured and which depends on the complex impedance. As described above, in one embodiment, a 20 kHz, 100 μA AC constant current signal is sourced along the path 60, as illustrated, from one connector (SOURCE (+), starting at node A) through the common node (node D) to a return patch electrode (, SOURCE (−), node B). The complex impedance sensor 58 is coupled to the sense connectors (SENSE (+), SENSE (−)), and is configured to determine the impedance across the path 62. For the constant current excitation signal of a linear circuit, the impedance will be proportional to the observed voltage developed across SENSE (+)/SENSE (−), in accordance with Ohm's Law: Z=V/I. Because voltage sensing is nearly ideal, the current flows through the path 60 only, so the current through path 62 (node D to node C) due to the excitation signal is effectively zero. Accordingly, when measuring the voltage along path 62, the only voltage observed will be where the two paths intersect (i.e. from node A to node D). Depending on the degree of separation of the two patch electrodes (i.e., those forming nodes B and C), an ever-increasing focus will be placed on the tissue volume nearest the tip electrode 12. If the patch electrodes are physically close to each other, the circuit pathways between the catheter tip electrode 12 and the patch electrodes will overlap significantly and impedance measured at the common node (i.e., node D) will reflect impedances not only at the interface of the catheter electrode 12 and tissue 16, but also other impedances between tissue 16 and the surface of body 17. As the patch electrodes are moved further part, the amount of overlap in the circuit paths decreases and impedance measured at the common node is only at or near the tip electrode 12 of catheter 14.

Figure 3:
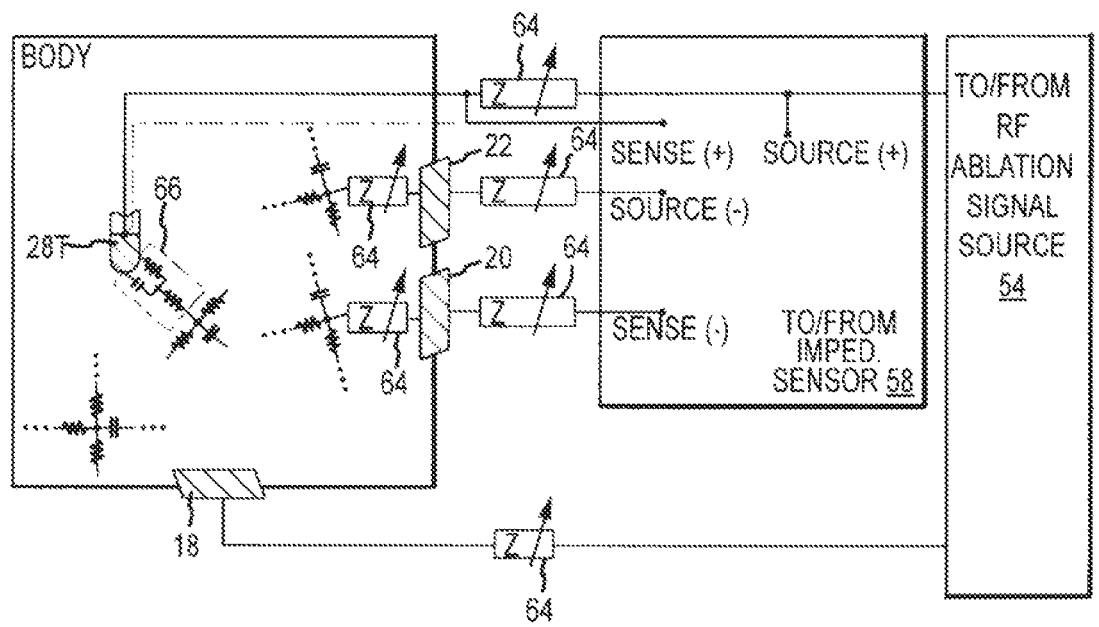
FIG. 3 is a diagrammatic and block diagram illustrating the approach in FIG. 2 in greater detail.

Referring now to FIG. 3, the concept illustrated in FIG. 2 is extended. FIG. 3 is a simplified schematic and block diagram of the three-terminal measurement arrangement of the invention. For clarity, it should be pointed out that the SOURCE (+) and SENSE (+) lines may be joined in the catheter connector 40 or handle 42 (as in solid line) or may remain separate all the way to the tip electrode (the SENSE (+) line being shown in phantom line from the handle 42 to the tip electrode 12). FIG. 3 shows in particular several sources of complex impedance variations, shown generally as blocks 64, that are considered "noise" because such variations do not reflect the physiologic changes in the tissue 16 or electrical coupling whose complex impedance is being measured. For reference, the tissue 16 whose complex impedance is being measured is that near and around the tip electrode 12 and is enclosed generally by a phantom-line box 66 (and the tissue 16 is shown schematically, in simplified form, as a resistor/capacitor combination). One object of the invention is to provide a measurement arrangement that is robust or immune to variations that are not due to changes in or around box 66. For example, the variable complex impedance boxes 64 that are shown in series with the various cable connections (e.g., in the SOURCE (+) connection, in the SOURCE (−) and SENSE (−) connections, etc.) may involve resistive/inductive variations due to cable length changes, cable coiling and the like. The variable complex impedance boxes 64 that are near the patch electrodes 20, 22, may be more resistive/capacitive in nature, and may be due to body perspiration and the like over the course of a study. As will be seen, the various arrangements of the invention are relatively immune to the variations in blocks 64, exhibiting a high signal-to-noise (S/N) ratio as to the complex impedance measurement for block 66.

Although the SOURCE (−) and SENSE (−) returns are illustrated in FIG. 3 as patch electrodes 20, 22, it should be understood that other configurations are possible. In particular, indifferent/dispersive return electrode 18 can be used as a return as well as another electrode 50, 52 on catheter 14, such as ring electrode 50 as described in commonly assigned U.S. patent application Ser. No. 11/966,232 filed on Dec. 28, 2007 and titled "SYSTEM AND METHOD FOR MEASUREMENT OF AN IMPEDANCE USING A CATHETER SUCH AS AN ABLATION CATHETER," the entire disclosure of which is incorporated herein by reference.

EP monitor 28 is provided display electrophysiology data including, for example, an electrogram. Monitor 28 is conventional in the art and may comprise an LCD or CRT monitor or another conventional monitor. Monitor 28 may receive inputs from ablation generator 24 as well as other conventional EP lab components not shown in the illustrated embodiment.

System 30 is provided for visualization, mapping and navigation of internal body structures. System 30 may comprise the system having the model name EnSite NavX™ and commercially available from St. Jude Medical, Inc. and as generally shown with reference to commonly assigned U.S. Pat. No. 7,263,397 titled "Method and Apparatus for Catheter Navigation and Location and Mapping in the Heart," the entire disclosure of which is incorporated herein by reference. System 30 may include an electronic control unit (ECU) 32 and a display device 34 among other components.

ECU 32 is provided to acquire values for first and second components of a complex impedance between the catheter tip electrode 12 and tissue 16 and to calculate a coupling index responsive to the values with the coupling index indicative of a degree of coupling between electrode 12 and tissue 16. ECU 32 may further calculate the coupling index responsive to a standardization value indicative of a deviation from a reference standard by a parameter associated with at least one of the body 17, the electrode 12 and another component of system 10. ECU 32 preferably comprises a programmable microprocessor or microcontroller, but may alternatively comprise an application specific integrated circuit (ASIC). ECU 32 may include a central processing unit (CPU) and an input/output (I/O) interface through which ECU 32 may receive a plurality of input signals including signals from sensor 58 of tissue sensing circuit 26 and generate a plurality of output signals including those used to control display device 34. In accordance with one aspect of the present invention, ECU 32 may be programmed with a computer program (i.e., software) encoded on a computer storage medium for determining a degree of coupling between an electrode on a catheter and tissue in a body. The program includes code for calculating a coupling index responsive to values for first and second components of the complex impedance between the catheter electrode 12 and tissue 16 with the coupling index indicative of a degree of coupling between the catheter electrode 12 and the tissue 16. The program may further include code for calculating the coupling index responsive to a standardization value indicative of a deviation from a reference standard by a parameter associated with at least one of body 17, electrode 12 and another component of system 10.

ECU 32 acquires one or more values for two component parts of the complex impedance from signals generated by sensor 58 of tissue sensing circuit 26 (i.e., the resistance (R) and reactance (X) or the impedance magnitude (|Z|) and phase angle ($\phi$) or any combination of the foregoing or derivatives or functional equivalents thereof). In accordance with one aspect of the present invention, ECU 32 combines values for the two components into a single coupling index that provides an improved measure of the degree of coupling between electrode 12 and tissue 16 and, in particular, the degree of electrical coupling between electrode 12 and tissue 16.

Validation testing relating to the coupling index was performed in a pre-clinical animal study. The calculated coupling index was compared to pacing threshold as an approximation of the degree of coupling. Pacing threshold was used for comparison because it is objective and particularly sensitive to the degree of physical contact between the tip electrode and tissue when the contact forces are low and the current density paced into the myocardium varies. In a study of seven swine (n=7, 59+/−3 kg), a 4 mm tip irrigated RF ablation catheter was controlled by an experienced clinician who scored left and right atrial contact at four levels (none, light, moderate and firm) based on clinician sense, electrogram signals, three-dimensional mapping, and fluoroscopic images. Several hundred pacing threshold data points were obtained along with complex impedance data, electrogram amplitudes and data relating to clinician sense regarding contact. A regression analysis was performed using software sold under the registered trademark "MINITAB" by Minitab, Inc. using the Log 10 of the pacing threshold as the response and various impedance parameters as the predictor. The following table summarizes the results of the analysis:

| Model | Regression Factors in Model | | | | | Regression $\hat{R}^2$ | |
|---|---|---|---|---|---|---|---|
| | | | | | | $\hat{R}^2$ | $\hat{R}^2$_adj |
| 1 | | | | | R1_mean (p < 0.001) | 43.60% | 43.50% |
| 2 | | | | | X1_mean (p < 0.001) | 35.70% | 35.50% |
| 3 | | | | X1_mean (p < 0.001) | R1_mean (p < 0.001) | 47.20% | 46.90% |
| 4 | | X1_stdev (p = 0.300) | R1_stdev (p = 0.155) | X1_mean (p < 0.001) | R1_mean (p < 0.001) | 48.70% | 48.00% |
| 5 | R1_P-P (p = 0.253) | X1_stdev (p = 0.280) | R1_stdev (p = 0.503) | X1_mean (p < 0.001) | R1_mean (p < 0.001) | 49.00% | 48.10% |

As shown in the table, it was determined that a mean value for resistance accounted for 43.5% of the variation in pacing threshold while a mean value for reactance accounted for 35.5% of the variation in pacing threshold. Combining the mean resistance and mean reactance values increased the predictive power to 46.90% demonstrating that a coupling index based on both components of the complex impedance will yield improved assessment of coupling between the catheter electrode 12 and tissue 16. As used herein, the "mean value" for the resistance or reactance may refer to the average of N samples of a discrete time signal $x_i$ or a low-pass filtered value of a continuous $x(t)$ or discrete $x(t_i)$ time signal. As shown in the table, adding more complex impedance parameters such as standard deviation and peak to peak magnitudes can increase the predictive power of the coupling index. As used herein, the "standard deviation" for the resistance or reactance may refer to the standard deviation, or equivalently root mean square (rms) about the mean or average of N samples of a discrete time signal $x_i$ or the square root of a low pass filtered value of a squared high pass filtered continuous $x(t)$ or discrete $x(t_i)$ time signal. The "peak to peak magnitude" for the resistance or reactance may refer to the range of the values over the previous N samples of the discrete time signal $x_i$ or the $k^{th}$ root of a continuous time signal $[abs(x(t))]^k$ that has been low pass filtered for sufficiently large k>2. It was further determined that, while clinician sense also accounted for significant variation in pacing threshold (48.7%)—and thus provided a good measure for assessing coupling—the combination of the coupling index with clinician sense further improved assessment of coupling (accounting for 56.8% of pacing threshold variation).

Because of the processing and resource requirements for more complex parameters such as standard deviation and peak to peak magnitude and because of the limited statistical improvement these parameters provided, it was determined that the most computationally efficient coupling index would be based on mean values of the resistance (R) and reactance (X). From the regression equation, the best prediction of pacing threshold—and therefore coupling—was determined to be the following equation (3):

$$ECI = R\text{mean} - 5.1 * X\text{mean} \quad (3)$$

where Rmean is the mean value of a plurality of resistance values and Xmean is the mean value of a plurality of reactance values. It should be understood, however, that other values associated with the impedance components such as a standard deviation of a component or peak to peak magnitude of a component which reflect variation of impedance with cardiac motion or ventilation can also serve as useful factors in the coupling index. Further, although the above equation and following discussion focus on the rectangular coordinates of resistance (R) and reactance (X), it should be understood that the coupling index could also be based on values associated with the polar coordinates impedance magnitude (|Z|) and phase angle ($\phi$) or indeed any combination of the foregoing components of the complex impedance and derivatives or functional equivalents thereof. Finally, it should be understood that coefficients, offsets and values within the equation for the coupling index may vary depending on among other things, the desired level or predictability, the species being treated and disease states. In accordance with the present invention, however, the coupling index will always be responsive to both components of the complex impedance in order to arrive at an optimal assessment of coupling between the catheter electrode 12 and tissue 16.

The above-described analysis was performed using a linear regression model wherein the mean value, standard deviation and/or peak to peak magnitude of components of the complex impedance were regressed against pacing threshold values to enable determination of an optimal coupling index. It should be understood, however, that other models and factors could be used. For example, a nonlinear regression model may be used in addition to, or as an alternative to, the linear regression model. Further, other independent measures of tissue coupling such as atrial electrograms could be used in addition to, or as an alternative to, pacing thresholds.

Validation testing was also performed in a human trial featuring twelve patients undergoing catheter ablation for atrial fibrillation. The patients were treated using an irrigated, 7 French radio frequency (RF) ablation catheter with a 4 mm tip electrode operating at a standard setting of a 50° C. tip temperature, 40 W power and 30 ml/min. flow rate (adjusted accordingly proximate the esophagus). An experienced clinician placed the catheter in the left atrium in positions of unambiguous non-contact and unambiguous contact (with varying levels of contact including "light," "moderate," and "firm") determined through fluoroscopic imaging, tactile feedback electrograms, clinician experience and other information. In addition to impedance, measurements of electrogram amplitudes and pacing thresholds were obtained for comparison. Each measure yielded corresponding changes in value as the catheter electrode moved from a no-contact position to a contact position. In particular, electrogram amplitudes increased from 0.14+/−0.16 to 2.0+/−1.9 mV, pacing thresholds decreased from 13.9+/−3.1 to 3.1+/−20 mA and the coupling index increased from 118+/−15 to 145+/−24 (with resistance increasing from 94.7+/−11.0 to 109.3+/−15.1Ω and reactance decreasing from −4.6+/−0.9 to −6.9+/−2Ω). Further, the coupling index increased (and resistance increased and reactance decreased) as the catheter electrode was moved from a "no-contact" (115+/−12) position to "light," (135+/−15) "moderate," (144+/−17) and "firm" (159+/−34) positions. These measurements further validate the use of the coupling index to assess coupling between the catheter electrode 12 and tissue 16. The calculated coupling index and clinician sense of coupling were again compared to pacing threshold as an approximation of the degree of coupling. A regression analysis was performed using a logarithm of the pacing threshold as the response and various impedance parameters and clinician sense as predictors. From this analysis, it was determined that clinician sense accounted for approximately 47% of the variability in pacing threshold. The addition of the coupling index, however, with clinician sense resulted in accounting for approximately 51% of the variability in pacing threshold—further demonstrating that the coupling index can assist clinicians in assessing coupling between the catheter electrode 12 and tissue 16.

Figure 4:
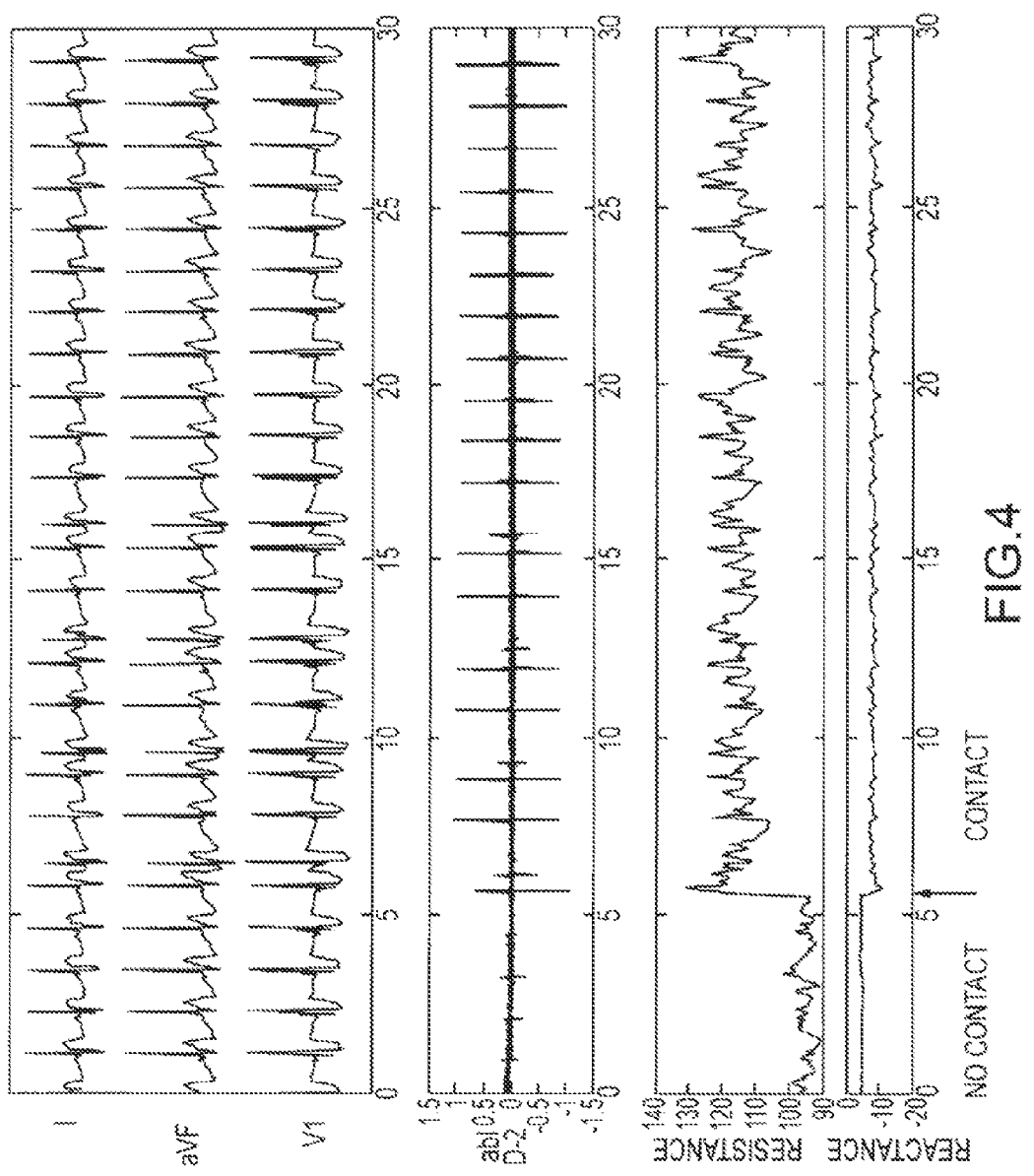
FIG. 4 is a series of diagrams illustrating complex impedance variations during atrial tissue ablation and cardiac tissue contact over thirty (30) seconds.
Figure 5:
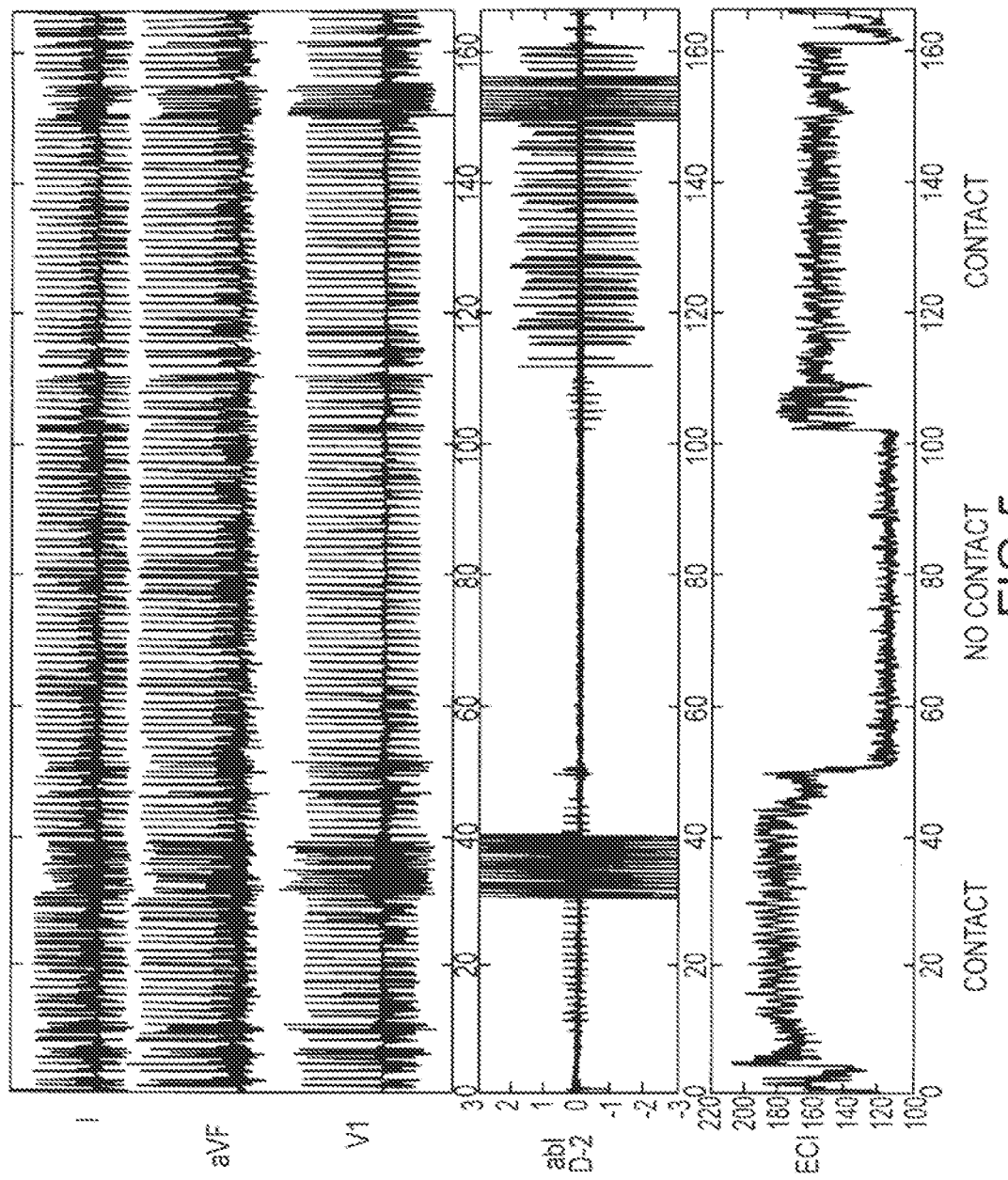
FIG. 5 is s series of diagrams illustrating variations in a coupling index during atrial tissue ablation and cardiac tissue contact over one hundred and sixty (160) seconds.

Referring now to FIGS. 4-5, a series of timing diagrams (in registration with each other) illustrate a comparison of atrial electrograms relative to changes in resistance and reactance (FIG. 4) and the composite coupling index (FIG. 5). As noted hereinabove, atrial electrograms are one traditional measurement for assessing coupling between the catheter electrode 12 and tissue 16. As shown in FIG. 4, the signal amplitude of the atrial electrogram increases when the catheter electrode 12 moves from a position of "no contact" to "contact" with tissue 16. Similarly, measured resistance (R) increases and reactance (X) decreases and become more variable (FIG. 4) and the calculated coupling index increases (FIG. 5), further demonstrating the utility of the coupling index in assessing coupling between electrode 12 and tissue 16.

The human validation testing also revealed that the coupling index varied depending on tissue types. For example, the coupling index tended to be higher when the catheter electrode was located inside a pulmonary vein than in the left atrium. As a result, in accordance with another aspect of the present invention, the coupling index may be used in identifying among tissue types (e.g., to identify vascular tissue as opposed to trabeculated and myocardial tissue). Further, because force sensors may not adequately estimate the amount of energy delivered into tissue in constrained regions such as the pulmonary vein or trabeculae, the inventive coupling index may provide a more meaningful measure of ablation efficacy than force sensors. In addition, in certain situations, it may be advantageous to utilize both a force sensor and the coupling index.

Impedance measurements are also influenced by the design of catheter 14 connection cables 56 or other factors. Therefore, the coupling index may preferably comprise a flexible equation in which coefficients and offsets are variable in response to design parameters associated with catheter 14. Catheter 14 may include a memory such as an EEPROM that stores numerical values for the coefficients and offsets or stores a memory address for accessing the numerical values in another memory location (either in the catheter EEPROM or in another memory). ECU 32 may retrieve these values or addresses directly or indirectly from the memory and modify the coupling index accordingly.

The physical structure of the patient is another factor that may influence impedance measurements and the coupling index. Therefore, ECU 32 may also be configured to offset or normalize the coupling index (e.g., by adjusting coefficients or offsets within the index) responsive to an initial measurement of impedance or another parameter in a particular patient. In addition, it may be beneficial to obtain and average values for the coupling index responsive to excitation signals generated by source 56 at multiple different frequencies.

In addition to the design of catheter 14 and the physical structure of the patient, variation in other components and/or characteristics of system 10 can impact impedance measurements and the coupling index. In accordance with one aspect of the present teachings, therefore, ECU 32 is configured to calculate the coupling index responsive to values for the components of a complex impedance between electrode 12 and tissue 16 and a standardization value indicative of a deviation from a reference standard by a parameter associated with at least one of body 17, electrode 12 and another component of system 10. Exemplary parameters may include the temperature, size, shape, surface area, body mass index, and electrolyte concentrations of body 17, the size of electrode 14, and the size and location of electrodes 18, 20, 22.

The coupling index may be generally represented by the following equation (4):

$$ECI = a * R\text{mean} + b * X\text{mean} + c \quad (4)$$

where Rmean is the mean value of a plurality of resistance values and Xmean is the mean value of a plurality of reactance values and a, b, and c are coefficients acting as standardization values permitting standardization of the coupling index by scaling or offset. The coefficients a, b, and c can be varied to address deviations from reference standards by a wide variety of parameters. For parameters associated with certain components of system 10, these deviations can be addressed by establishing initial or default values for the coefficients in the memory or code in ECU 32. In particular, impedance measurements may be impacted by circuit design (e.g., by employing amplifiers with different gains or power supplies with different voltage limits) and by the chosen format of values resulting from analog to digital conversion (e.g., the number of bits, signed vs. unsigned, integer vs. floating point, etc.). Changes in impedance measurements resulting from changes in parameters associated with such components in system 10 can be quantified and used to adjust the coefficients in equation (4). The equation (3) ECI=Rmean−5.1*Xmean recited hereinabove is one variation of equation (4) in which the coefficient a equals 1, the coefficient b equals −5.1 and the coefficient c equals 0 as determined based on testing one exemplary system 10.

For parameters relating to other components of system 10, deviations from reference standards can be addressed by retrieving information relating to the component and adjusting the coefficients in equation (4) accordingly. As referenced hereinabove, changes in catheter 14 impacting impedance measurements can be compensated for by adjusting the coefficients using information retrieved from an EEPROM in catheter 14. It has been determined, for example, that that the size of electrode 12 on catheter 14 impacts impedance measurements. In particular, smaller electrodes (e.g. 2.5 mm) result in larger impedance measurements and in larger changes in impendence when moving between contact and non-contact positions relative to larger electrodes (e.g., 4 mm or 8 mm). An EEPROM in catheter 14 may include numerical values for the coefficients in equation (4) based on the size of the electrode (and/or other parameters associated with catheter 14) or store a memory address for accessing the numerical values in another memory location (either in the catheter EEPROM or in another memory). ECU 32 may retrieve these values or addresses directly or indirectly from the memory and modify the coupling index accordingly.

Variations in certain parameters from a reference standard may be addressed dynamically during operation of system 10. Body temperature and fluid conductivity in body 17 are two exemplary parameters. As body temperature increases, the conductivity of saline in catheter 14 increases and the resistive component of impedance decreases. Body temperature may be measured using a conventional temperature sensor on catheter 14. In response to the measured temperature, a standardization value (e.g., one of coefficients a, b, and c in equation (4)) can be adjusted to compensate for a deviation in the measured temperature from a reference standard. The standardization value may be applied as an offset (e.g., coefficient c in equation (4)) to the values of complex impedance (e.g., Rmean and Xmean in equation (4)) or as a scaling of one or both values (e.g., coefficient a or b in equation (4)). For example, if the reference standard body temperature is 37° C. and the conductivity of saline increases by 2% as temperature increases by each degree Celsius (and the resistive impedance decreases by 2% as temperature increases by each degree Celsius), ECU 32 may calculate the coupling index ECI by adjusting the offset in equation (4) (assuming that coefficients a, b, and c are previously optimized for a body temperature of 37° C.) as set forth in equation (5):

$$ECI = a*Rmean + b*Xmean + (c + 0.02*a(T-37)) \quad (5)$$

where T is the measured body temperature. Alternatively, ECU 32 may calculate the coupling index ECI by adjusting the scaling of the resistive component of the complex impedance (because the temperature dependence of impedance in saline is almost entirely resistive) in equation (4) as set forth in equation (6):

$$ECI = a(1 + 0.02(T-37))*Rmean + b*Xmean + c \quad (6)$$

where T again represents the measured body temperature.

Figure 8:
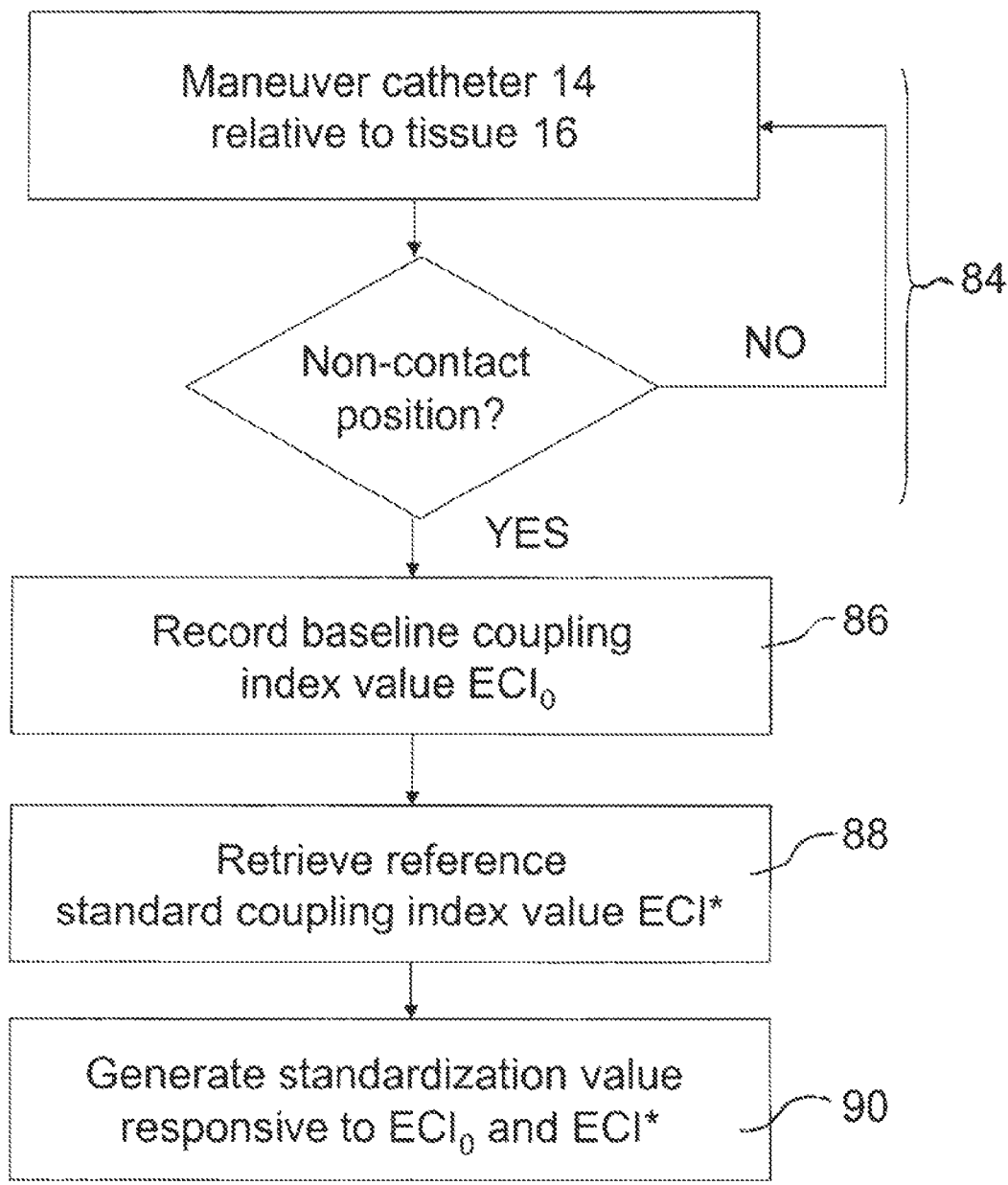
FIG. 8 is a flow chart illustrating one embodiment of a method in accordance with the present teachings.

For certain parameters that impact impedance—particularly those associated with body 17, but also cabling and placement of electrodes 18, 20, 22—variations relative to reference standards are not easily measured or controlled. Referring to FIG. 8, in accordance with one aspect of the present teachings, a method for generating a standardization value is provided that accounts for variations in these types of parameters. The method may begin with the step 84 of moving catheter 14 relative to tissue 16 (e.g., within a cardiac chamber) until catheter 14 is in a non-contact position with tissue 16. The non-contact position of catheter 14 relative to tissue 16 may be identified, for example, based on a low value for the coupling index, electrogram amplitude or contact force or visually using fluoroscopy. The method may continue with the step 86 of recording a baseline or "non-contact" value $ECI_0$ for the coupling index while the catheter is in the "non-contact" position and the step 88 of retrieving a reference standard value of the coupling index ECI*. The reference coupling index ECI* may be obtained from a memory in ECU 32 and may represent an average or mean value for the coupling index in a non-contact position across a predetermined population. Alternatively, the reference coupling index ECI* may be obtained by inserting catheter 14 into a calibration apparatus to simulate a non-contact position. The method may continue with the step 90 of generating a standardization value responsive to the baseline coupling index $ECI_0$ and the reference coupling index ECI*—for example, based on the difference between the baseline coupling index $ECI_0$ and the reference coupling index ECI* (i.e. $ECI*-ECI_0$). The standardization value may again be applied as an offset to the values for the components of complex impedance or as a scaling of one or both values.

Figure 6:
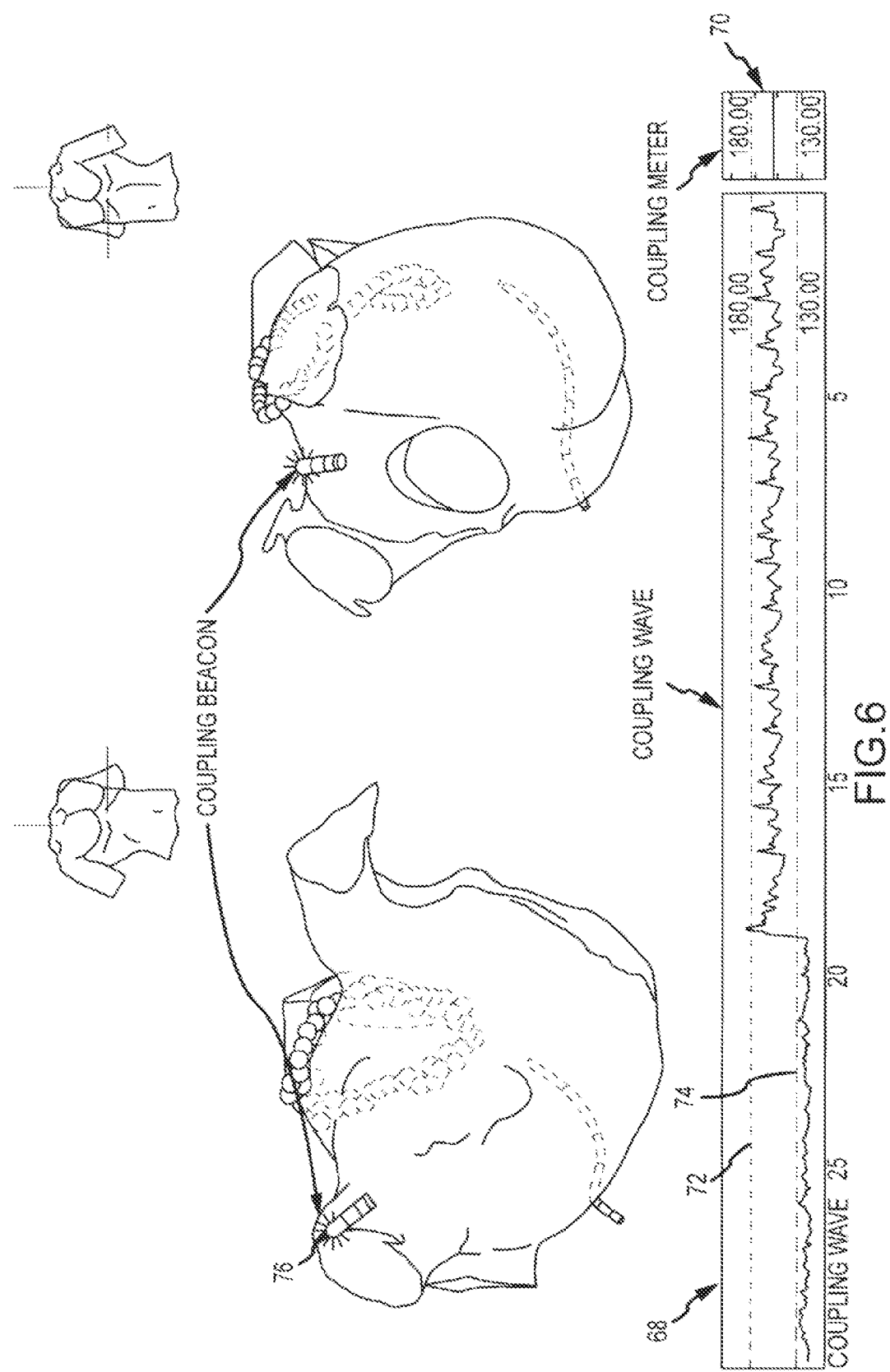
FIG. 6 is a screen display illustrating possible formats for presenting a coupling index to a clinician.

Referring now to FIG. 6, display device 32 is provided to present the coupling index in a format useful to the clinician. Device 32 may also provide a variety of information relating to visualization, mapping and navigation as is known in the art including measures of electrical signals, two and three dimensional images of the tissue 16 and three-dimensional reconstructions of the tissue 16. Device 32 may comprise an LCD monitor or other conventional display device. In accordance with another aspect of the present invention, the coupling index may be displayed in one or more ways designs to provide easy interpretation and correlation to tissue contact for the clinician. Referring to FIG. 6, the coupling index may be displayed as a scrolling waveform 68. The coupling index may also be displayed as a meter 70 which displays the one second average value of the coupling index. For either the scrolling waveform 68 or meter 70, upper and lower thresholds 72, 74 may be set (either pre-programmed in ECU 32 or input by the user using a conventional I/O device). Characteristics of the waveform 68 and/or meter 70 may change depending upon whether the value of the coupling index is within the range set by the thresholds (e.g., the waveform 68 or meter 70 may change colors such as from green to red if the value of the coupling index moves outside of the range defined by the thresholds). Changes to the coupling index may also be reflected in changes to the image of the catheter 14 and/or catheter electrode 12 on display device 34. For example, the catheter electrode 12 may be displayed on the screen (including within a two or three dimensional image or reconstruction of the tissue) as a beacon 76. Depending on the value of the coupling index, the appearance of the beacon 76 may change. For example, the color of the beacon 76 may change (e.g., from green to red) and/or lines may radiate outwardly from the beacon 76 as the index falls above, below or within a range of values.

In summary, the degree of coupling between a catheter electrode 12 and tissue 16 may be assessed through several method steps in accordance with one embodiment of the invention. First, an excitation signal is applied between electrode 12 and a reference electrode such as patch electrode 22 between connectors SOURCE (+) and SOURCE (−) along a first path 60 (see FIG. 2). As discussed above, signal source 56 of tissue sensing circuit 26 may generate the excitation signal at a predetermined frequency or frequencies. This action induces a voltage along path 62 between electrode 12 and another reference electrode such as patch electrode 20. The voltage may be measured by sensor 58 which resolves the sensed voltage into component parts of the complex impedance at tissue 16. As a result, ECU 32 acquires values for the components of the complex impedance. ECU 32 then calculates a coupling index responsive to the values that is indicative of a degree of coupling between the electrode 12 and tissue 16. The index may then be presented to a clinician in a variety of forms including by display on display device 34 as, for example, a waveform 68, meter 70 or beacon 76.

A coupling index formed in accordance with the teaching of the present invention may be useful in a variety of applications. As shown in the embodiment illustrated in FIG. 1, the coupling index can be used as part of a system 10 for ablation of tissue 16. The coupling index provides an indication of the degree of electrical coupling between tip electrode 12 and tissue 16 thereby assisting in the safe and effective delivery of ablation energy to tissue 16.

The coupling index may further provide an indication of the proximity or orientation of the tip electrode 12 to adjacent tissue 16. Referring to FIGS. 1 and 2, signal source 56 of sensing circuit 26 may generate excitation signals across source connectors SOURCE (+) and SOURCE (−) defined between tip electrode 12 and patch electrode 22 and also between ring electrode 50 and patch electrode 22. Impedance sensor 58 may then measure the resulting voltages across sense connectors SENSE (+) and SENSE (−)) defined between tip electrode 12 and patch electrode 20 and also between ring electrode 50 and patch electrode 22. ECU 32 may compare the measured values directly or, more preferably, determine a coupling index for each of electrodes 12, 50 responsive to the measured values and compare the two indices. The comparison provides an indication of orientation of tip electrode 12. For example, a rise in the measured impedance or coupling index for both electrodes 12, 50 may indicate that electrode 12 is parallel to tissue 16. A rise in the measured impedance or coupling index for electrode 12, but not for electrode 50, may indicate that electrode 12 is perpendicular to tissue 16. Differences between the measured impedance or coupling index for electrodes 12, 50 may indicate that electrode 12 is disposed at an angle (as well as the degree of that angle) relative to tissue 16. It should be understood that electrode 50 is used for exemplary purposes only. Similar results could be obtained with other electrodes disposed proximate tip electrode 12 or from using a split tip electrode.

The present invention may also be used as a proximity sensor. As an electrode such as electrode 12 approaches tissue 16 the impedance changes as does the coupling index. Further, for some electrode configurations, this change is independent of the angle at which the electrode is 12 is disposed relative to tissue 16. The coupling index is therefore indicative of the proximity of the electrode 12 to tissue 16. In some applications, the general position (with a frame of reference) and speed of the tip of catheter 14 and electrode 12 is known (although the proximity of electrode 12 to tissue 16 is unknown). This information can be combined to define a value (the "coupling index rate") that is indicative of the rate of change in the coupling index as electrode 12 approaches tissue 16 and which may provide an improved measure of the proximity of the electrode 12 to tissue 16. This information can be used, for example, in robotic catheter applications to slow the rate of approach prior to contact and also in connection with a transseptal access sheath having a distal electrode to provide an indication that the sheath is approaching (and/or slipping away from) the septum. The coupling index rate can also be used to filter or smooth variation in signals resulting from cardiac cycle mechanical events.

Figure 7:
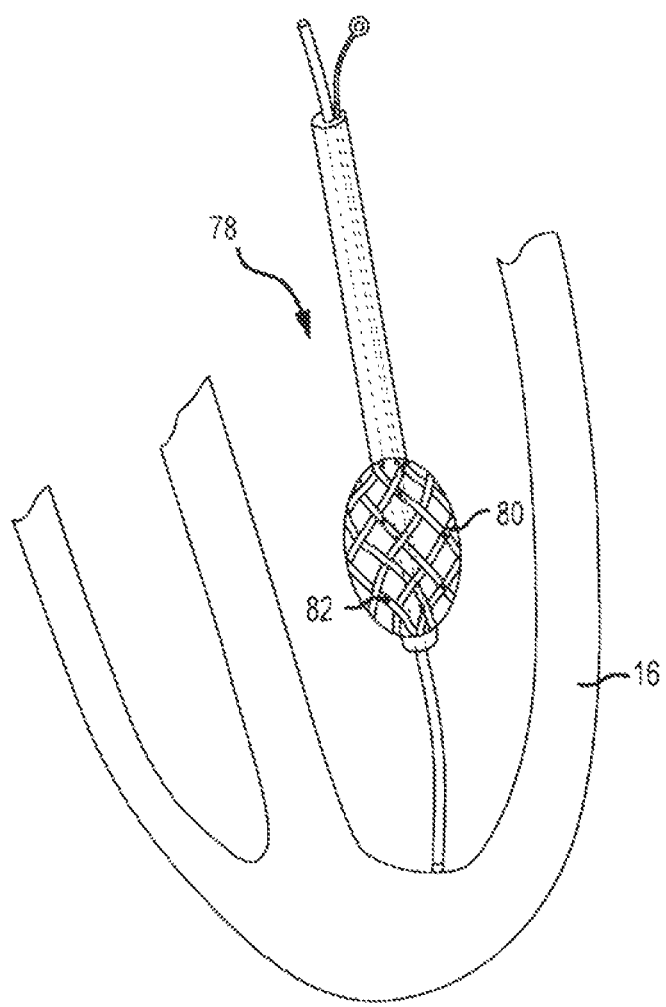
FIG. 7 is a diagrammatic view of a multi-electrode, array catheter illustrating one embodiment of a system in accordance with present teachings.

The present invention may also find application in systems having multiple electrodes used for mapping the heart or other tissues, obtaining electrophysiological (EP) information about the heart or other tissues or ablating tissue. Referring to FIG. 7, one example of an EP catheter 78 is shown. EP catheter 78 may be a non-contact mapping catheter such as the catheter sold by St. Jude Medical, Atrial Fibrillation Division, Inc. under the registered trademark "ENSITE ARRAY." Alternatively, catheter 78 may comprise a contact mapping catheter in which measurements are taken through contact of the electrodes with the tissue surface. Catheter 78 includes a plurality of EP mapping electrodes 80. The electrodes 80 are placed within electrical fields created in body 17 (e.g., within the heart). The electrodes 80 experience voltages that are dependent on the position of the electrodes 80 relative to tissue 16. Voltage measurement comparisons made between electrodes 80 can be used to determine the position of the electrodes 80 relative to tissue 16. The electrodes 80 gather information regarding the geometry of the tissue 16 as well as EP data. For example, voltage levels on the tissue surface over time may be projected on an image or geometry of the tissue as an activation map. The voltage levels may be represented in various colors and the EP data may be animated to show the passage of electromagnetic waves over the tissue surface. Information received from the electrodes 80 can also be used to display the location and orientation of the electrodes 80 and/or the tip of EP catheter 78 relative to tissue 16. Electrodes 80 may be formed by removing insulation from the distal end of a plurality of braided, insulated wires 82 that are deformed by expansion (e.g. through use of a balloon) into a stable and reproducible geometric shape to fill a space (e.g., a portion of a heart chamber) after introduction into the space.

In the case of contact mapping catheters, the coupling index can be used to determine which electrodes 80 are in contact with or in close proximity to tissue 16 so that only the most relevant information is used in mapping the tissue 16 or in deriving EP measurements or so that different data sets are more properly weighted in computations. As with the systems described hereinabove, signal source 56 of sensing circuit 26 may generate excitation signals across source connectors SOURCE (+) and SOURCE (−) defined between one or more electrodes 80 and patch electrode 22. Impedance sensor 58 may then measure the resulting voltages across sense connectors SENSE (+) and SENSE (−)) defined between each electrode 80 and patch electrode 20. ECU 32 may then determine which electrodes 80 have the highest impedance and/or coupling index to determine the most relevant electrodes 80 for purposes of mapping or EP measurements. Similarly, in the case of a multiple electrode ablation catheter (not shown), the coupling index can be used to determine which electrodes are in contact with tissue 16 so that ablation energy is generated through only those electrodes, or can be used to adjust the power delivered to different electrodes to provide sufficient power to fully ablate the relevant tissue.

The present invention also permits simultaneous measurements by multiple electrodes 80 on catheter 78. Signals having distinct frequencies or multiplexed in time can be generated for each electrode 80. In one constructed embodiment, for example, signals with frequencies varying by 200 Hz around a 20 kHz frequency were used to obtain simultaneous distinct measurements from multiple electrodes 80. Because the distinct frequencies permit differentiation of the signals from each electrode 80, measurements can be taken for multiple electrodes 80 simultaneously thereby significantly reducing the time required for mapping and/or EP measurement procedures. Microelectronics permits precise synthesis of a number of frequencies and at precise quadrature phase offsets necessary for a compact implementation of current sources and sense signal processors. The extraction of information in this manner from a plurality of transmitted frequencies is well known in the field of communications as quadrature demodulation. Alternatively, multiple measurements can be accomplished essentially simultaneously by multiplexing across a number of electrodes with a single frequency for intervals of time less than necessary for a significant change to occur.

A system, article of manufacture, and method in accordance with the present teachings offers one or more of a number of advantages. First, they provide a true measure of impedance at the interface of the electrode and the target tissue and, therefore, provide a more qualitative assessment of coupling between the electrode and the tissue. In particular, the system, article, and method exclude accumulated impedance between the target tissue and the body surface as well as impedance resulting from external factors unrelated to the patient such as cable length, coiling, and the like. The measurement is also standardized such that it will provide a similar measure despite variation in parameters associated with the body, the electrode, and the system as a whole. Further, the system, article of manufacture and method provide an indicator of coupling (i.e., the coupling index) in a format that allows easy interpretation and correlation to tissue contact by the clinician. As a result, ablation procedures can be conducted more efficiently and with higher success rates and fewer complications.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for assessing a degree of coupling between a first electrode and a tissue in a body, comprising:
   a complex impedance sensor; and,
   an electronic control unit configured to acquire values for first and second components of a complex impedance between said first electrode and said tissue responsive to one or more signals output by said complex impedance sensor and to calculate a first coupling index responsive to said values and a first variable parameter associated with said system, said first coupling index indicative of a degree of coupling between said first electrode and said tissue.

2. The system of claim 1 wherein said electronic control unit is further configured, in calculating said first coupling index, to apply an offset to said values of said first and second components of said complex impedance responsive to said first variable parameter.

3. The system of claim 1 wherein said electronic control unit is further configured, in calculating said first coupling index, to scale at least one of said values of said first and second components of said complex impedance responsive to said first variable parameter.

4. The system of claim 1 wherein said electronic control unit is further configured, in calculating said first coupling index to scale one of said values of said first and second components of said complex impedance responsive to said first variable parameter and scale another of said values of said first and second components of said complex impedance responsive to one of said first variable parameter and a second variable parameter associated with said system.

5. The system of claim 1 wherein said electronic control unit is configured to calculate said first coupling index in accordance with the equation $aR+bX+c$ wherein R and X correspond to said values for said first and second components of said complex impedance between said first electrode and said tissue and a, b, and c correspond to a first standardization value indicative of a deviation from a reference standard by said first variable parameter, a second standardization value indicative of a deviation from a reference standard by one of said first variable parameter and a second variable parameter associated with said system, and a third standardization value indicative of a deviation from a reference standard by one of said first variable parameter, said second variable parameter and a third variable parameter associated with said system.

6. The system of claim 5 wherein R comprises a mean value of a plurality of values for said first component of said complex impedance and X comprises a mean value for a plurality of values for said second component of said complex impedance.

7. The system of claim 1 wherein said first variable parameter comprises one or more of a temperature of said body, an electrolyte concentration in said body, and a size of said first electrode.

8. The system of claim 1 wherein said electronic control unit is further configured to identify a type of said tissue responsive to said first coupling index.

9. The system of claim 1 wherein said electronic control unit is further configured to determine at least one of a proximity of said first electrode to said tissue and an orientation of said first electrode relative to said tissue responsive to said first coupling index.

10. The system of claim 1 wherein said electronic control unit is further configured to:
   acquire values for first and second components of a complex impedance between a second electrode and said tissue responsive to one or more signals output by said complex impedance sensor and to calculate a second coupling index responsive to said values for said first and second components of said complex impedance between said second electrode and said tissue and one of said first variable parameter and a second variable parameter associated with said system, said second coupling index indicative of a degree of coupling between said second electrode and said tissue; and,
   determine which of said first and second electrodes has a higher impedance responsive to said first and second coupling indeces.

11. The system of claim 1, further comprising a display configured to display a representation of said first coupling index.

12. The system of claim 11 wherein a characteristic of said representation assumes one of a first state and a second state depending on a value of said first coupling index relative to a threshold value.

13. The system of claim 1, further comprising a display configured to display a representation of said first electrode wherein a characteristic of said representation assumes one of a first state and a second state depending on a value of said first coupling index relative to a threshold value.

14. A method for assessing a degree of coupling between a first electrode and a tissue in a body, comprising:
   acquiring values for first and second components of a complex impedance between said first electrode and said tissue response to one or more signals output by a complex impedance sensor; and,
   calculating a first coupling index responsive to said values and a first variable parameter associated with a system controlling said first electrode, said first coupling index indicative of a degree of coupling between said first electrode and said tissue.

15. The method of claim 14, wherein calculating said first coupling index includes applying an offset to said values of said first and second components of said complex impedance responsive to said first variable parameter.

16. The method of claim 14, wherein calculating said first coupling index includes scaling at least one of said values of said first and second components of said complex impedance responsive to said first variable parameter.

17. The method of claim 14, wherein calculating said first coupling index includes:
   scaling of one of said values of said first and second components of said complex impedance responsive to said first variable parameter; and scaling another of said values of said first and second components of said complex impedance responsive to one of said first variable parameter and a second variable parameter associated with said system.

18. The method of claim 14 wherein said first coupling index in calculated in accordance with the equation aR+bX+c wherein R and X correspond to said values for said first and second components of said complex impedance between said first electrode and said tissue and a, b, and c correspond to a first standardization value indicative of a deviation from a reference standard by said first variable parameter, a second standardization value indicative of a deviation from a reference standard by one of said first variable parameter and a second variable parameter associated with said system, and a third standardization value indicative of a deviation from a reference standard by one of said first variable parameter, said second variable parameter and a third variable parameter associated with said system.

19. The method of claim 18 wherein R comprises a mean value of a plurality of values for said first component of said complex impedance and X comprises a mean value for a plurality of values for said second component of said complex impedance.

20. The method of claim 14 wherein said first variable parameter comprises one or more of a temperature of said body, an electrolyte concentration in said body, and a size of said first electrode.

21. The method of claim 14, further comprising one or more of identifying a type of said tissue, determining a proximity of said first electrode to said tissue, and determining an orientation of said first electrode relative to said tissue responsive to said first coupling index.

22. The method of claim 14, further comprising:
acquiring values for first and second components of a complex impedance between a second electrode and said tissue responsive to one or more signals output by said complex impedance sensor;
calculating a second coupling index responsive to said values for said first and second components of said complex impedance between said second electrode and said tissue and one of said first variable parameter and a second variable parameter associated with said system, said second coupling index indicative of a degree of coupling between said second electrode and said tissue; and,
determining which of said first and second electrodes has a higher impedance responsive to said first and second coupling indeces.

23. The method of claim 14, further comprising displaying a representation of said first coupling index wherein a characteristic of said representation assumes one of a first state and a second state depending on a value of said first coupling index relative to a threshold value.

24. The method of claim 14, further comprising displaying a representation of said first electrode wherein a characteristic of said representation of said first electrode assumes one of a first state and a second state depending on a value of said first coupling index relative to a threshold value.

* * * * *